US010107751B2

(12) United States Patent
Scherer et al.

(10) Patent No.: US 10,107,751 B2
(45) Date of Patent: Oct. 23, 2018

(54) HIGH-ACCURACY MID-IR LASER-BASED GAS SENSOR

(71) Applicant: Thermo Fisher Scientific (Bremen) GmbH, Bremen (DE)

(72) Inventors: James J. Scherer, Hillsborough, CA (US); Joshua B. Paul, Palo Alto, CA (US); Hans-Juerg Jost, Helsinki (FI)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 0 days.

(21) Appl. No.: 15/595,366

(22) Filed: May 15, 2017

(65) Prior Publication Data

US 2017/0248517 A1    Aug. 31, 2017

Related U.S. Application Data

(62) Division of application No. 13/229,511, filed on Sep. 9, 2011, now Pat. No. 9,651,488.

(51) Int. Cl.
*G01N 21/35* (2014.01)
*G01N 21/61* (2006.01)
(Continued)

(52) U.S. Cl.
CPC ......... *G01N 21/61* (2013.01); *G01N 21/0332* (2013.01); *G01N 21/05* (2013.01);
(Continued)

(58) Field of Classification Search
CPC ........ G01N 21/35; G01N 21/59; G01N 21/61; G01N 21/3504; G01N 21/39; G01N 21/031
(Continued)

(56) References Cited

U.S. PATENT DOCUMENTS 4,205,913 A     6/1980  Ehrfeld et al.
4,627,067 A *  12/1986  Barr, Jr. .................... H01S 3/03
                                                                      372/55
(Continued)

OTHER PUBLICATIONS

Bamford et al., "Widely tunable rapid-scanning mid-infrared laser spectrometer for industrial gas process stream analysis," Applied Optics, vol. 46 (19), pp. 3958-3968, (2007).
(Continued)

*Primary Examiner* — David Porta
*Assistant Examiner* — Gisselle Gutierrez
(74) *Attorney, Agent, or Firm* — Thomas F. Cooney

(57) ABSTRACT

A gas sensor system is provided, comprising: a gas cell operable so as to receive a sample gas; a vacuum system fluidically coupled to the gas cell operable to maintain the sample gas within the gas cell at a sub-ambient pressure; a pressure sensor operable to sense a pressure of the sample gas; a thermally insulated enclosure having the gas cell therein; a heat source or heat exchanger operable to influence an interior temperature of the thermally insulated enclosure; a light source within the thermally insulated enclosure operable to provide a mid-infrared (mid-IR) light into and through the gas cell; a photodetector within the thermally insulated enclosure operable to receive the attenuated mid-IR; and a control system electronically coupled to the vacuum system and to the pressure sensor operable to maintain the sample gas within the gas cell at the predetermined pressure to within one torr (1 Torr).

23 Claims, 20 Drawing Sheets

(51) Int. Cl.
  *G01N 21/3504* (2014.01)
  *G01N 21/39* (2006.01)
  *G01N 21/05* (2006.01)
  *G01N 33/00* (2006.01)
  *G01N 21/03* (2006.01)

(52) U.S. Cl.
  CPC ......... *G01N 21/3504* (2013.01); *G01N 21/39* (2013.01); *G01N 33/004* (2013.01); *G01N 33/0037* (2013.01); *G01N 21/031* (2013.01); *Y02A 50/245* (2018.01)

(58) Field of Classification Search
  USPC ................................ 250/338.1; 356/51, 437
  See application file for complete search history.

(56) References Cited

U.S. PATENT DOCUMENTS

| | | | | |
|---|---|---|---|---|
| 4,749,276 A * | 6/1988 | Bragg | ................. | G01N 21/031 250/343 |
| 5,331,409 A * | 7/1994 | Thurtell | ................. | G01N 21/39 250/345 |
| 5,400,173 A * | 3/1995 | Komine | ................. | G02F 1/3532 359/326 |
| 5,577,061 A * | 11/1996 | Hasenberg | ................. | H01S 5/20 372/45.012 |
| 5,616,923 A | 4/1997 | Rich et al. | | |
| 5,838,008 A * | 11/1998 | Esler | ................. | G01J 3/28 250/339.07 |
| 5,912,910 A * | 6/1999 | Sanders | ................. | G02F 1/3534 359/326 |
| 6,064,488 A * | 5/2000 | Brand | ................. | G01N 21/39 356/437 |
| 6,134,004 A * | 10/2000 | Reagen | ................. | G01N 21/03 356/450 |
| 6,188,475 B1 | 2/2001 | Inman et al. | | |
| H1965 H | 6/2001 | Burns et al. | | |
| 6,344,648 B1 * | 2/2002 | Boucher | ................. | G01N 21/39 250/339.13 |
| 7,050,170 B2 * | 5/2006 | Chilese | ................. | G01N 21/39 250/352 |
| 7,154,595 B2 * | 12/2006 | Paldus | ................. | G01J 3/44 356/73 |
| H2197 H | 8/2007 | Gord et al. | | |
| 7,265,842 B2 * | 9/2007 | Paldus | ................. | G01N 21/39 250/343 |
| 7,535,573 B2 * | 5/2009 | Kachanov | ................. | G01J 3/42 356/437 |
| 7,646,485 B2 * | 1/2010 | Tan | ................. | G01J 3/28 356/437 |
| 7,810,376 B2 * | 10/2010 | Koulikov | ................. | G01N 1/405 73/23.31 |
| 2002/0177248 A1 * | 11/2002 | McCann | ................. | B82Y 20/00 438/22 |
| 2003/0202550 A1 * | 10/2003 | Goyal | ................. | B82Y 20/00 372/45.01 |
| 2004/0000643 A1 * | 1/2004 | Karlsson | ................. | G01N 21/61 250/339.13 |
| 2005/0077028 A1 * | 4/2005 | Oikawa | ................. | F28D 15/02 165/80.4 |
| 2005/0225840 A1 * | 10/2005 | Drasek | ................. | G01N 21/39 359/333 |
| 2005/0226296 A1 * | 10/2005 | Botez | ................. | B82Y 20/00 372/45.01 |
| 2005/0243876 A1 * | 11/2005 | Kung | ................. | G02F 1/39 372/21 |
| 2006/0011844 A1 * | 1/2006 | Oka | ................. | G01N 21/3504 250/343 |
| 2006/0025835 A1 * | 2/2006 | Calcott | ................. | B82Y 20/00 607/86 |
| 2006/0245461 A1 * | 11/2006 | Islam | ................. | H01S 3/094003 372/75 |
| 2007/0076209 A1 | 4/2007 | Baer et al. | | |
| 2007/0081162 A1 * | 4/2007 | Roller | ................. | G01N 21/3504 356/437 |
| 2007/0133625 A1 * | 6/2007 | Ahn | ................. | H01S 3/0675 372/6 |
| 2007/0133626 A1 * | 6/2007 | Ahn | ................. | H01S 3/0675 372/6 |
| 2008/0223109 A1 * | 9/2008 | Nitta | ................. | G01N 21/3504 73/23.2 |
| 2008/0231841 A1 * | 9/2008 | Nitta | ................. | G01N 21/3504 356/73 |
| 2008/0259340 A1 | 10/2008 | Prasad et al. | | |
| 2009/0028193 A1 * | 1/2009 | Islam | ................. | H01S 5/0064 372/6 |
| 2009/0028197 A1 * | 1/2009 | Arnone | ................. | B82Y 20/00 372/32 |
| 2009/0185190 A1 | 7/2009 | Weinberger et al. | | |
| 2009/0296743 A1 * | 12/2009 | Islam | ................. | H01S 3/2316 372/3 |
| 2009/0304034 A1 * | 12/2009 | Mirov | ................. | H01S 3/06 372/20 |
| 2010/0053720 A1 * | 3/2010 | Magari | ................. | G01J 1/32 359/244 |
| 2010/0110438 A1 | 5/2010 | Furtaw | | |
| 2010/0111122 A1 * | 5/2010 | Pushkarsky | ................. | H01S 5/4012 372/32 |
| 2010/0163733 A1 * | 7/2010 | Prasad | ................. | G01N 21/3518 250/345 |
| 2010/0329291 A1 * | 12/2010 | Sanders | ................. | G02F 1/3534 372/22 |
| 2012/0287418 A1 * | 11/2012 | Scherer | ................. | G01N 21/61 356/51 |
| 2013/0044323 A1 | 2/2013 | Liu et al. | | |

OTHER PUBLICATIONS

Chen et al., "Continuous-wave mid-infrared laser sources based on difference frequency generation," C R Physique (2007), doi:10.1016/j.crhy.2007.09.011, pp. 1-22.

D. G. Lancaster et al., "Portable fiber-coupled diode-laser-based sensor for multiple trace gas detection," Appl. Phys. B 69, pp. 459-465, (1999).

D. G. Lancaster et al., "Real-time measurements of trace gases using a compact difference-frequency-based sensor operating at 3.5 μm," Appl. Phys. B 67, pp. 339-345, (1998).

D. Mazzotti et al., "Difference-frequency radiation around 4.3 μm for high sensivity and sub-Doppler spectroscopy of CO2," Advanced Semiconductor Lasers and Their Applications (ASLA 1999), vol. 31 of OSA Trends in Optics and Photonics Series (TOPS), pp. 122-127.

D. Richter et al., "Compact mid-infrared trace gas sensor based on difference-frequency generation of two diode lasers in periodically poled LiNbO3," Appl. Phys. B 67, pp. 347-350, (1998).

D. Richter et al., "Tunable, fiber coupled spectrometer based on difference-frequency generation in periodically poled lithium niobate," Advanced Solid State Lasers, M. Fejer, H. Injeyan, and U. Keller, eds., vol. 26 of OSA Trends in Optics and Photonics (Optical Society of America, 1999), paper WC5., p. 1-4.

F. K. Tittel et al., "Novel Diode Laser-Based Sensors for Gas Sensing Applications," Laser Physics, vol. 10, No. 1, (2000), pp. 348-354.

K. Fradkin et al., "Tunable midinfrared source by difference frequency generation in bulk periodically poled KTiOPO4," Applied Physics Letters, vol. 74 (7), pp. 914-916, (1999).

K. P. Petrov et al., "Detection of CO in air by diode-pumped 4.6-μm difference-frequency generation in quasi-phase-matched LiNbO3," Optics Letters, vol. 21 (1), pp. 86-88, (1996).

Kosterov et al., "Thermoelectrically cooled quantum-cascade-laser-based sensor for the continuous monitoring of ambient atmospheric carbon monoxide," Applied Optics, vol. 41 (6), pp. 1169-1173 (2002).

M. Erdelyi et al., "13CO2/12CO2 isotopic ratio measurements using a difference frequency-based sensor operating at 4.35 μm," Appl. Phys. B 75, pp. 289-295 (2002).

(56) References Cited

OTHER PUBLICATIONS

Mark G. Allen, "Diode Laser Absorption Sensors for Gas Dynamic and Combustion Flows," Measurement Science and Technology (1998), http://www.iop.org/Journals/mt, pp. 1-61.
Richter, et al., "Development of an Automated Diode-Laser-Based Multicomponent Gas Sensor", Applied Optics, vol. 39 (24), 2000, pp. 4444-4450.
T. Kelz et al., "Detection of CO in Air Using Diode Laser Pumped Difference—Frequency Generation in a Modular Setup," J. Quant. Spectrosc. Radiat. Transfer vol. 61 (5), pp. 591-601, (1999).
Tittel, et al., "Mid-Infrared Laser Applications in Spectroscopy", in "Solid-State Mid-Infrared Laser Sources", Springer Berlin Heidelberg, XP055197064, 2003, vol. 89, pp. 445-516.
Toepfer et al., "Room-temperature mid-infrared laser sensor for trace gas detection," Applied Optics, vol. 36, (30), pp. 8042-8049, (1997).

* cited by examiner

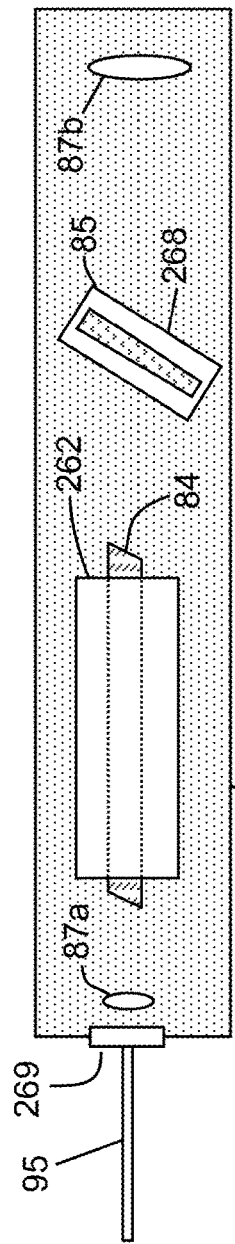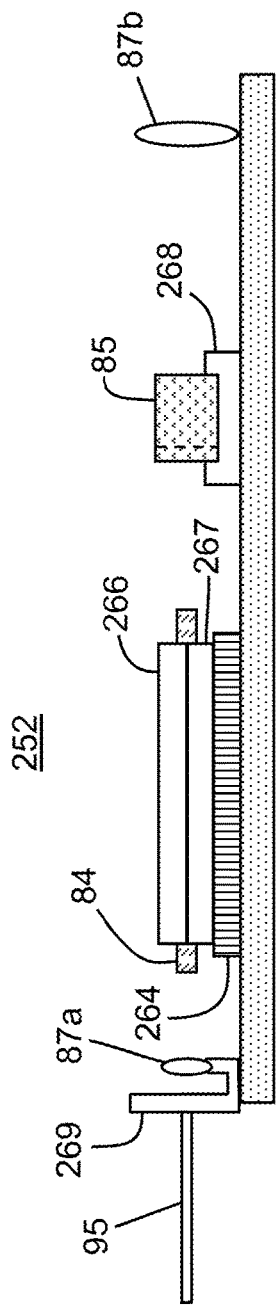

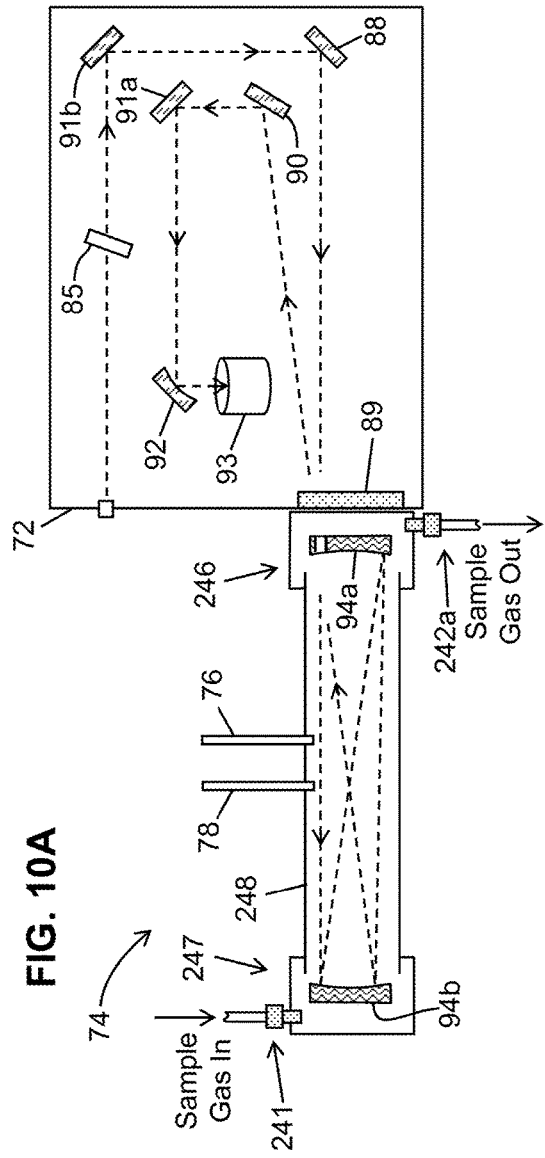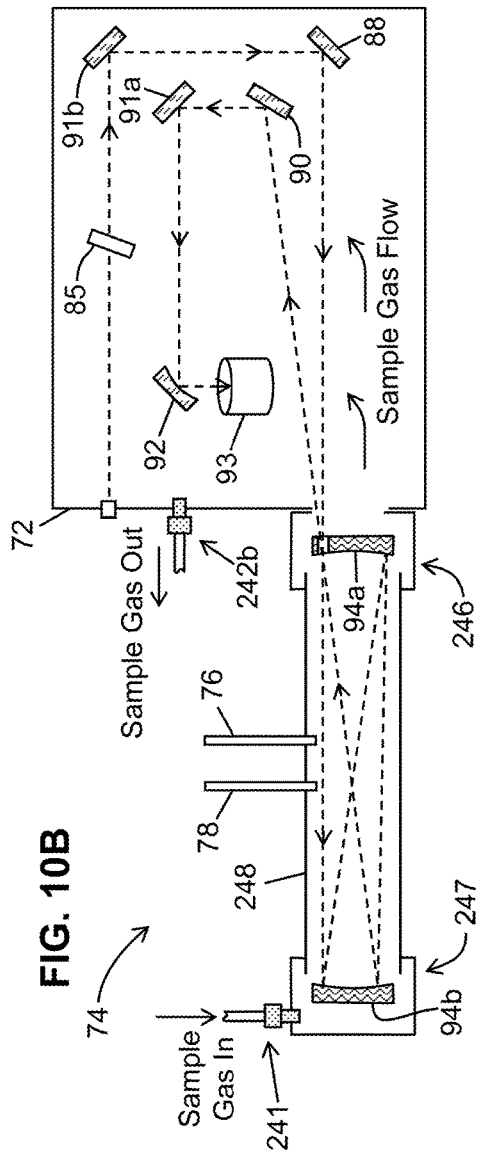

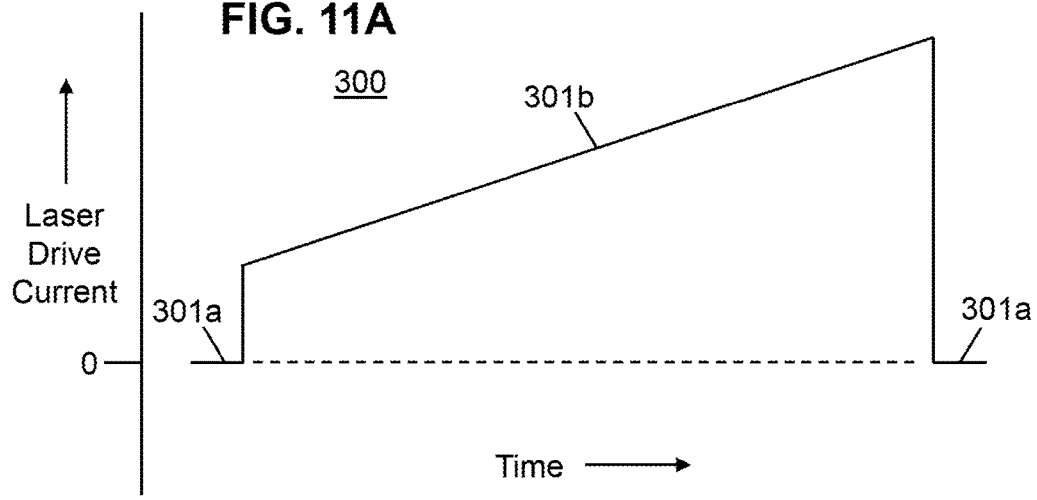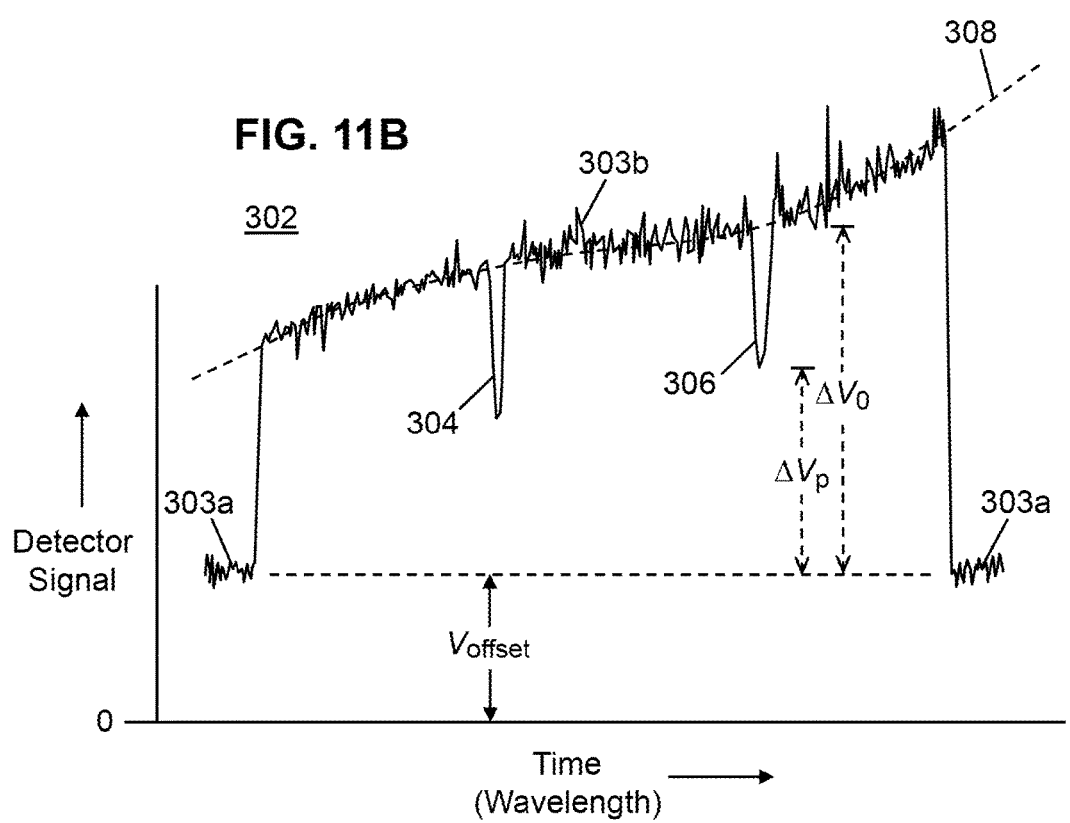

HIGH-ACCURACY MID-IR LASER-BASED GAS SENSOR

CROSS REFERENCE TO RELATED APPLICATIONS

This application is a Divisional of and claims, under 35 USC § 120, priority to and the benefit of the filing date of co-pending U.S. patent application Ser. No. 13/229,511, now U.S. Pat. No. 9,651,488, filed on Sep. 9, 2011, the disclosure of which is hereby incorporated by reference herein in its entirety as if set forth fully herein.

FIELD OF THE INVENTION

This invention generally relates to gas sensors for use in environmental air monitoring or industrial air monitoring and relates, more particularly, to such gas sensors that are capable of monitoring the variation, over time, of the concentration of a target gas species by measuring absorption of infrared light attributable to the target gas species.

BACKGROUND OF THE INVENTION

The need for highly accurate, optically based trace gas sensors is relevant to many disciplines, comprising greenhouse gas monitoring, pollution monitoring, industrial process monitoring, industrial air quality monitoring and benchtop chemical analysis systems. Field determinations of gas species dispersal patterns from, for instance, landfills, agricultural lands and highways comprise an important aspect of greenhouse gas monitoring and pollution monitoring. Trace gases of interest in this regard include nitric oxide (NO), nitrous oxide ($N_2O$), carbon monoxide (CO), carbon dioxide ($CO_2$), sulfur dioxide ($SO_2$) and methane ($CH_4$), among others.

Gas absorption spectroscopy is an important technique for field monitoring of trace gas species, such as those listed above. Such spectroscopic measurements are performed by measuring the percentage of light which passes through a gas sample at given light wavelengths. The technique makes use of the fact that particular gases exhibit characteristic light absorption responses as the wavelength of the light passing through the gas is varied. Gas species can thus be identified by these responses.

Trace gas species identification is typically performed by identifying the presence of one or more absorption "lines" attributable to the species in a gas sample. An absorption line is a narrow band of light wavelengths (or, correspondingly, frequencies or wavenumbers) at which the gas absorbs or attenuates light. A given gas usually has a number of absorption lines at different wavelengths (or alternatively, frequencies or wavenumbers). A typical gas sensor system may make a determination of the molecular concentration, s, of a target gas in a gas sample by making two measurements at a wavelength corresponding to an absorption line: (1) a measurement of the intensity of light transmitted through the target gas; and (2) a measurement of the intensity of light transmitted along the same path in the absence of the target gas. The ratio of these two measurements is defined as transmittance.

Pending regulations will require that greenhouse gases be monitored at various emissions sources, beginning with the thousands of sites that are presently required to monitor other air pollutants. Detecting ambient trace levels of various greenhouse gases—expected at parts-per-million (ppm) or parts-per-billion (ppb) levels—with high confidence (e.g., 1000:1 fidelity) will require high accuracy sensors that achieve ppb detection levels in real-time. For example, to measure the vertical flux of a pollutant or greenhouse gas from a source on the ground to the atmosphere at large, a gas sensor device may be placed, together with a wind speed device and other atmospheric measuring instruments (e.g., a thermometer and a barometer), at an elevated location above the putative source such as, for instance, on a tower above a pasture land. For a fully turbulent flux, the average vertical flux, F, of the gas species may be calculated, by combining measurements of vertical wind speed, w, and molecular concentration, s, of a target gas species, according to the "eddy flux" (or "eddy covariance") equation, $$F = \overline{\rho_a w s} \approx \overline{\rho_a w' s'} \qquad \text{Eq. 1}$$

in which $\rho_a$ is mean air density, w' and s' are the time derivatives of vertical wind speed and target gas concentration, respectively, and the overbar symbols represents mean values. The approximation on the right-hand side of the above equation resolves a practical experimental difficulty of measuring air density simultaneously with and at the same repetition rate as measurements of wind speed and gas concentration. However, in order to use this approximation, the time derivative of the concentration must be calculated. Since the expected typical concentrations of various target species are at the parts-per-million (ppm) or parts-per-billion (ppb) level, accurate calculations of s' require the precision of these measurements to be at least at the level of several tens of ppb (or better). Furthermore, since vertical wind speed can change on time scales of much less than one second, simultaneous precise gas concentration measurements must be available on the same time scale.

Fast instruments are particularly needed for such eddy covariance measurements. Established IR spectroscopic sensor technologies such as non-dispersed infrared absorption-based instruments cannot achieve the required accuracy levels, because the presence of interferents, such as water vapor, confounds such measurements. Moreover, many existing gas sensor systems employ cumbersome, ultra-high reflectivity optical multipass cells such as astigmatic Herriot or Cavity Ringdown cells in order to obtain measurements in the near infrared (0.7-3 µm), and are thus sensitive to optical contamination of the mirror surfaces that can result from commonly occurring trace level particulates and other contaminants. Thus, although there presently exists an open-path methane sensor that operates in the near-infrared, it requires periodic cleaning of the mirror surfaces via rinsing the multipass cell optics with a solution while spinning the mirror at high speed, thereby adding consumables, size, and cost to the sensor. Additionally, the size of this conventional sensor is not ideal, as local heating of the sample gas may occur.

The mid-infrared (mid-IR) range of the electromagnetic spectrum (wavelengths in the range of 3-8 µm, is of much greater use for such trace gas measurements, since most important trace gas species of interest exhibit, within this region, pronounced absorption lines that may be differentiated from lines attributable to water vapor ($H_2O$) and other interfering species. Typically, the mid-IR absorption lines are much stronger than the absorption lines found in the near-IR. For instance, methane exhibits several strong rotationally-resolved (ro-vibrational) and interference-free infrared absorption lines near 3.3 µm. Likewise, carbon dioxide exhibits similarly useful lines near 4.3 µm and carbon monoxide and nitrogen dioxide exhibit similarly useful lines near 4.6 µm.

Lasers are the most appropriate light sources for measuring transmittance at the wavelengths of rotationally resolved infrared absorption lines. Lasers can provide intense, monochromatic light comprising a wavelength which, in some cases, can be tuned to match an absorption line feature and which comprises a bandwidth that is narrower than the bandwidth of the absorption line feature. Diode lasers are preferred for field portable instruments because of their small size, durability and low power requirements.

Unfortunately, conventional diode lasers cannot be used directly in many important mid-IR spectrographic applications because they produce light frequencies in the 1 to 1.5 µm range (near infrared). So-called "lead salt" diode lasers are available with emission at the required wavelength ranges. However, these lasers are not suitable for use in field-portable gas sensors because they are expensive and because they require cryogenic cooling which adds additional complexity and limits the ability of the gas sensor to run unattended. So-called "quantum cascade" lasers are also available but are not generally suitable for portable gas sensor systems because of their relatively high cost, low yield and inability to access the 3-4 micron spectral region. Light sources which provide a shifted frequency by means of an optical parametric oscillator (OPO) are presently too expensive and bulky to be considered for use in a field portable instrument.

As a result of the above considerations, light sources which produce mid-IR light through difference frequency generation (DFG) are the only presently available light sources that are suitable for use in field-portable automatically operating gas sensor systems. Such light sources may utilize two (or more) near-IR light sources together with a non-linear crystal to generate mid-IR light. However, gas sensor systems based on mid-IR absorption and having the necessary sensitivity, precision and stability required for long-term unattended field measurement of gas fluxes have not yet been described. The present invention addresses such a need.

SUMMARY

The present disclosure teaches various gas sensors for measuring, with high accuracy, the concentration of a given trace gas species in a gas sample. These gas sensors are based on optical absorption of middle infrared light that is specifically generated in a unique difference frequency generation (DFG) laser source. The laser source itself has numerous attributes that makes it a superior choice over alternative laser or other middle infrared light sources, especially with regard to the spectral purity, stability, and propagation qualities of the light generated. When this light source is coupled with suitable optical imaging and detection subcomponents, high performance analog control electronics, microprocessor control, and software, a high accuracy and highly specific autonomous sensor results.

Embodiments in accordance with the present teachings exhibit significantly reduced sensitivity to contaminants (e.g., by a factor of ten to one thousand) as they do not require an effectively long path length (otherwise achieved via the ultra-high reflectivity multipass cell) to achieve a detectable absorption level. Fundamentally, this is due to the intrinsically stronger middle infrared absorption that is monitored in the present invention compared to that of the near-infrared absorption that is monitored in other instruments. Methane absorption is nearly 200 times stronger in the middle infrared compared the near-infrared, thus enabling instruments in accordance with the present teachings to be much more robust while achieving as sensitive or better accuracy and precision than other approaches.

According to various embodiments, in order to determine the concentration of the species of interest, a direct optical absorption measurement is performed. The sample gas flows through a gas cell, and a mid-infrared laser source is directed through the gas cell. After the mid-infrared light exits the gas cell, it is directed onto a detector. As the mid-IR laser wavelength is tuned, absorption peaks from the species of interest can be measured. The signal from the detector is amplified, captured, digitized and analyzed by a computer. From the calculated strengths of the absorption line(s), the concentration of the species of interest is determined. The sample gas flows continuously through the gas cell, and the sensor makes continuous measurements of the species concentration in real time.

In practice, the laser light may be generated in the middle infrared DFG source, optically imaged into a gas interrogation region that may be either (i) an optical cell that is enclosed and used with a pump to introduce the gas or (ii) completely open to the surrounding environment without the need for a pump, and detected after passing through the sample to measure attenuation of the light as the laser frequency is changed to reveal the absorption spectrum. Specifically, the rovibrational (rotationally resolved) absorption spectrum of a target gas is detected with high fidelity as a function of frequency in what is commonly described in the art as a high resolution "direct absorption" measurement. The method does not require frequency or wavelength modulation of the laser at high frequencies (KHz) as is commonly employed in conventional approaches to achieve sensitivity or to overcome other limitations encountered in those approaches. The stable frequency and amplitude output of the laser source enables a simple direct absorption approach to be used, in part due to the ability to uniquely and directly determine the "zero level" of the absorption spectrum with high fidelity, which is not done in frequency or wavelength modulated approaches.

The sensor employs non-cryogenic photovoltaic detectors in the middle infrared that are combined with low-noise signal amplifiers, which, when properly mated, operate at a time bandwidth that enables rapid acquisition of the spectrum without distortion of the intrinsic absorption lineshape. Accurate determination of the associated integrated absorption fraction with respect to the laser energy zero-point at high speed provides a favorable duty cycle for the sensor, while also providing the ability to measure absorption in cases where spectral features can interfere with one another. In such cases, frequency or wavelength modulated approaches can fail in accurately determining the associated absorption intensity and hence accurate determination of the concentration of the target molecule. Embodiments in accordance with the present teachings are capable of ppt-level detection in timescales of less than a minute and single digit ppb-level detection in a few seconds. In various embodiments, the gas sensor employs several stabilization features that reduce system drift due to changes in ambient pressure and temperature. This stabilization reduces calibration intervals and associated calibration gas consumption. The present invention effectively eliminates the need for what is known as "zero gas" as the zero-point of the laser is effectively measured with each scan of the laser, which is performed at hundreds of Hz to kHz.

Accordingly, in one aspect, a gas sensor system for detecting and measuring the concentration of a gaseous molecular species within an environment having an ambient temperature and an ambient pressure is provided, the system comprising: a gas cell operable so as to receive the sample gas from the environment; a vacuum system fluidically coupled to the gas cell operable to maintain the sample gas within the gas cell at a predetermined pressure less than the ambient pressure; a pressure sensor operable to sense a pressure of the sample gas within the gas cell; a thermally insulated enclosure having the gas cell disposed therein; a heat source or heat exchanger operable to influence a temperature of the interior of the thermally insulated enclosure; a light source within the thermally insulated enclosure operable to provide a mid-infrared (mid-IR) light into the gas cell so as to be transmitted through the sample gas therein, wherein a wavelength of the mid-IR light coincides with a rotationally resolved absorption line of the gaseous molecular species; a photodetector within the thermally insulated enclosure operable to receive the mid-IR light transmitted through the sample gas in the gas cell; and a control system electronically coupled to the vacuum system and to the pressure sensor operable to maintain the sample gas within the gas cell at the predetermined pressure to within one torr (1 Torr).

In various embodiments, a temperature sensor and a control system electronically coupled to both the heat source or heat exchanger and the temperature sensor may serve to maintain the sample gas within the gas cell at a predetermined temperature to within one degree Kelvin (1° K). The predetermined temperature may be greater than the ambient temperature, such as within a range between about 30° C. to about 40° C. In some embodiments, the heat source or heat exchanger may comprise a thermoelectric element disposed within an aperture of the thermally insulated enclosure that is operable to either transfer heat into or out of the thermally insulated enclosure. A first and a second heat sink and fan assembly—disposed outside of and within the thermally insulated enclosure, respectively—may be provided in thermal contact with the thermoelectric element.

In various embodiments, the gas sensor system may further include a laser module within the thermally insulated enclosure, the light source or a portion thereof being disposed within the laser module; an optical module within the thermally insulated enclosure, the photodetector being disposed within the optical module, the optical module being optically coupled to the gas cell; and one or more optical fibers coupled to the laser module and to the optical module, wherein the one or more optical fibers are operable to direct light supplied from the light source into the optical module.

The light source may include a first and a second laser operable to provide, respectively, a first near-infrared (near-IR) light having a first wavelength and a second near-IR light having a second wavelength; a wavelength division multiplexer (WDM) optically coupled to the first laser and to the second laser and operable to receive the first and second near-IR lights therefrom; an optically non-linear crystal optically coupled to the WDM—possibly by means of one or more intervening optical fibers—and operable to receive the first and second near-IR lights therefrom and to generate the mid-IR light by difference frequency generation; and an optical filter optically coupled to the non-linear crystal and operable to transmit the mid-IR light while blocking transmission of the first and second near-IR lights. Either or both of the first and second lasers may comprise a diode laser or diode lasers. In such a case, a laser diode current driver may be provided that is operable to repeatedly modulate a drive current supplied to one of the first and second diode lasers such that a wavelength of the mid-IR light repeatedly traverses across a wavelength range of the rotationally resolved optical absorption line. Such embodiments may further include a digitizer electronically coupled to an output of the photodetector such that an output of the photodetector is digitized at each of a plurality of discrete time points during each modulation of the drive current so as to generate a plurality of digital detector signal values corresponding to a direct absorption spectrum; and a digital memory storage device operable to store the plurality of digital detector signal values.

In various embodiments, the first laser may emit a light having a wavelength within the range of 1000-1100 nm and the second laser may emit light having a wavelength with the range of 1500-1600 nm. In various other embodiments, the first laser may emit a light having a wavelength within the range of 1100-1200 nm and the second laser may emit light having a wavelength with the range of 1500-1600 nm. In various embodiments, the wavelength of the mid-IR light is within the range of approximately 3.0 microns to 4.8 microns.

In various embodiments, the gaseous molecular species may be chosen from the group consisting of carbon monoxide (CO), nitrous oxide ($N_2O$) and carbon dioxide ($CO_2$) and a center wavelength of the rotationally resolved absorption line is within the range of approximately 4.2 microns to 4.7 microns. In some embodiments, the gaseous molecular species is methane ($CH_4$) and a center wavelength of the rotationally resolved absorption line is within the range of approximately 3.2 microns to 3.4 microns. In some embodiments, the gaseous molecular species is carbon monoxide (CO) and a center wavelength of the rotationally resolved absorption line is within the range of approximately 4.57 microns to 4.65 microns. In some embodiments, the gaseous molecular species is nitrous oxide ($N_2O$) and a center wavelength of the rotationally resolved absorption line is within the range of approximately 4.510 microns to 4.555 microns.

In various embodiments, the gas cell may be fluidically coupled to the optical module such that, in operation, the sample gas flows from the gas cell into the optical module. In various other embodiments, a window may be provided between the gas cell and the optical module, such that the sample gas exhausts through an outlet port of the gas cell.

In another aspect, there is provided a method for detecting and measuring the concentration of a gaseous molecular species within an environment having an ambient temperature and an ambient pressure, the method comprising: (a) providing a light source capable of providing an emitted mid-IR light whose wavelength may be caused to traverse across the wavelength range of a rotationally resolved absorption line of the gaseous molecular species; (b) providing a gas cell; (c) providing a temperature-stabilized optical system for directing the mid-IR light from the light source into the gas cell so as to pass therethrough and, subsequently, from the gas cell to a photodetector; (d) providing a system for stabilizing the pressure of a sample gas flowing through the gas cell at a pressure less than the ambient pressure to within one torr (1 Torr); (e) providing a system for stabilizing the temperature of the sample gas flowing through the sample gas cell at a sample gas temperature greater than the ambient temperature to within one degree Kelvin (1° K); (f) causing the sample gas from the environment to flow through the gas cell at the sample gas pressure and the sample gas temperature; (g) operating the light source so as to cause the wavelength of the emitted mid-IR light to repeatedly traverse across the wavelength range of the rotationally resolved absorption line; (h) operating the optical system so as to cause the emitted mid-IR light to pass through and be attenuated by the sample gas in the gas cell and so as to cause the attenuated mid-IR light to pass to the photodetector; (i) detecting the attenuated mid-IR light by the detector at each of a plurality of discrete data points, each data point corresponding to a particular wavelength during a wavelength traverse; (j) constructing a direct absorption spectrum of the rotationally resolved absorption line from the plurality of data points; and (k) determining the concentration of the gaseous molecular species from the direct absorption spectrum.

The step (a) listed above may include the steps of: (a1) providing a first diode laser capable of providing a first near-IR light comprising a first frequency within a first frequency range; (a2) providing a second diode laser capable of providing a second near-IR light comprising a second frequency within a second frequency range, wherein the frequency of the second near-IR light may be tuned within the second frequency range, wherein the first and second frequency ranges are such that there exists a range of operationally achievable differences between the first and second frequencies that spans a frequency range of the rotationally resolved absorption line; and (a3) providing a non-linear crystal operable to receive the first and second near-IR lights and generate the mid-IR light. In such instances, the step (g) listed above may comprise the steps of: (g1) setting a drive current supplied to the second diode laser to zero so as to extinguish emission of the mid-IR light; (g2) setting the drive current supplied to the second diode laser to a non-zero value corresponding to a starting wavelength of the mid-IR light; and (g3) varying the drive current supplied to the second diode laser such that the mid-IR wavelength continuously varies from the starting wavelength to an ending wavelength, wherein the starting wavelength and the ending wavelength span the wavelength range of the rotationally resolved absorption line. Some embodiments may include a further step of: (g4) varying the drive current supplied to the second diode laser such that the mid-IR wavelength continuously varies from the ending wavelength to the starting wavelength.

The step (c) listed above may comprise the steps of: (c1) providing a thermally insulated enclosure; (c2) providing components of the optical system within the thermally insulated enclosure; (c3) providing a thermoelectric element within an aperture of the thermally insulated enclosure for transferring heat either into or out of the thermally insulated enclosure; (c4) providing a first and a second heat sink and fan assembly in thermal contact with the thermoelectric element and disposed outside of and within the thermally insulated enclosure, respectively; (c5) providing a temperature sensor with the thermally insulated enclosure; and (c6) providing temperature controller circuitry in electrical communication with the temperature sensor and the thermoelectric element, the temperature controller circuitry providing a current to the thermoelectric element based on an electronic signal received from the temperature sensor. In such instances, the step (e) listed above may comprise the steps of: (e1) positioning the gas cell within the thermally insulated enclosure; and (e2) causing the temperature controller to maintain the interior of the thermally insulated enclosure at the sample gas temperature.

In various embodiments, the step (d) listed above may comprise the steps of: (d1) providing a sample gas inlet port at a first end of the gas cell in fluid communication with the environment; (d2) providing a sample gas outlet port at a second end of the gas cell; (d3) providing a vacuum pump in fluidic communication with the sample gas outlet port and with a sample gas exhaust port; (d4) providing a pressure transducer in fluidic communication with the interior of the gas cell; and (d5) providing pressure controller circuitry in electrical communication with the pressure transducer and the vacuum pump, the pressure controller circuitry the pumping rate of the vacuum pump to vary based on an electronic signal received from the pressure transducer. In various embodiments, the step (j) listed above may comprise the steps of: (j1) determining a null detector response corresponding to no emission of the mid-IR light by the light source; (j2) subtracting the null detector response pointwise from the plurality of data points; (j3) fitting a model polynomial baseline using a subset of the plurality of data points outside of the wavelength range of the rotationally resolved absorption line; and (j4) subtracting, pointwise, the value of each of the plurality of data points from the value of the fitted polynomial calculated at the wavelength of each respective data point.

BRIEF DESCRIPTION OF THE DRAWINGS

The above noted and various other aspects of the present invention will become apparent from the following description which is given by way of example only and with reference to the accompanying drawings, not necessarily drawn to scale, in which:

FIGS. 8A-8B are a schematic plan and elevation views of a crystal, filter and lens assembly for difference-frequency generation in accordance with various embodiments of the present teachings;

FIG. 10A is a schematic illustration of a first alternative configuration of sample gas flow within a gas sensor in accordance with the present teachings;

FIG. 10B is a schematic illustration of a second alternative configuration of sample gas flow within a gas sensor in accordance with the present teachings;

FIG. 11A is a graph of a single cycle of an exemplary repetitive laser current-sweep waveform as applied to a laser of a light source of a gas sensor system in accordance with the present teachings;

FIG. 11B is a graph of an example of a detector signal as may be generated by a gas sensor system in accordance with the present teachings upon application of the current-sweep waveform of FIG. 10A to a laser of a light source of the system;

DETAILED DESCRIPTION

The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described. To appreciate the features of the present invention in greater detail, please refer to FIGS. 1-16 in conjunction with the following discussion.

System Configurations

Figure 1:
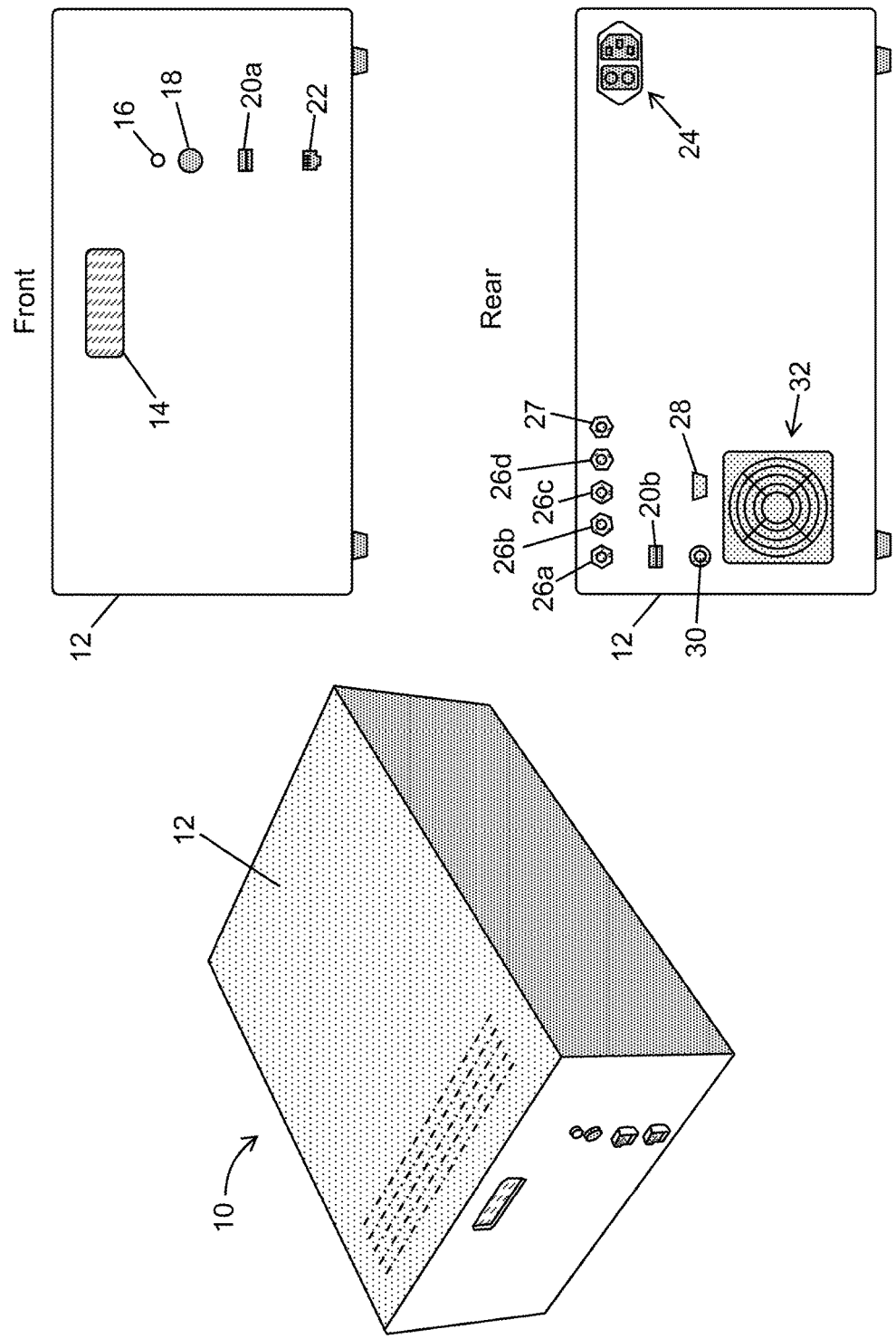
FIG. 1 is a set of external views of a gas sensor in accordance with the present teachings.

FIG. 1 is a set of external views—including perspective, front and rear views—of a gas sensor system in accordance with the present teachings. The illustrated gas sensor system 10 includes a chassis 12 that houses internal electronics, computer components, lasers, optics, a gas cell (measurement cell), a vacuum pump, a gas flow meter, sensors for temperature, pressure and gas flow rate, and associated electronic couplings and gas tubing interconnections. Externally, the system may provide a display window 14 for indicating instrument status or the value of a gas concentration measurement, a power button 18, a power indicator light 16, an AC power electrical connector port 24, a BNC jack 30 and a cooling fan 32. Sample or calibration gas is provided by means of one or more gas inlet ports 26a, 26b, 26c, 26d and is exhausted, after passing through the system, through a gas exhaust port 27. An internal gas manifold (not shown) may receive input sample or gas from one or more of the gas inlet ports 26a-26d. The optional BNC jack 30 may be employed to output an analog signal proportional to the gas concentration. This feature may be used to make the output of the system 10 compatible with older conventional gas sensors that provide an analog output that may be connected to a data logger or a strip chart recorder.

The gas sensor system 10 may include, internally, all or most components of a computer system, such as the internal components of a personal or desk computer including a motherboard with a microprocessor, cache memory, ROM memory, random access memory such as a hard disk, optical disk drive or flash memory, an operating system, control software, etc. Accordingly, the system 10 may provide various external communication ports at its front and rear panels for sending information to and receiving information from the internal computer system. For instance such external communication ports may include Universal Serial Bus (USB) ports 20a, 20b, for connecting a keyboard, an external memory device, etc. to the system; an Ethernet port 22 for connecting the internal computer system to an external network or to other computers and a VGA port 28 for providing detailed visual information display to a user.

Figure 2:
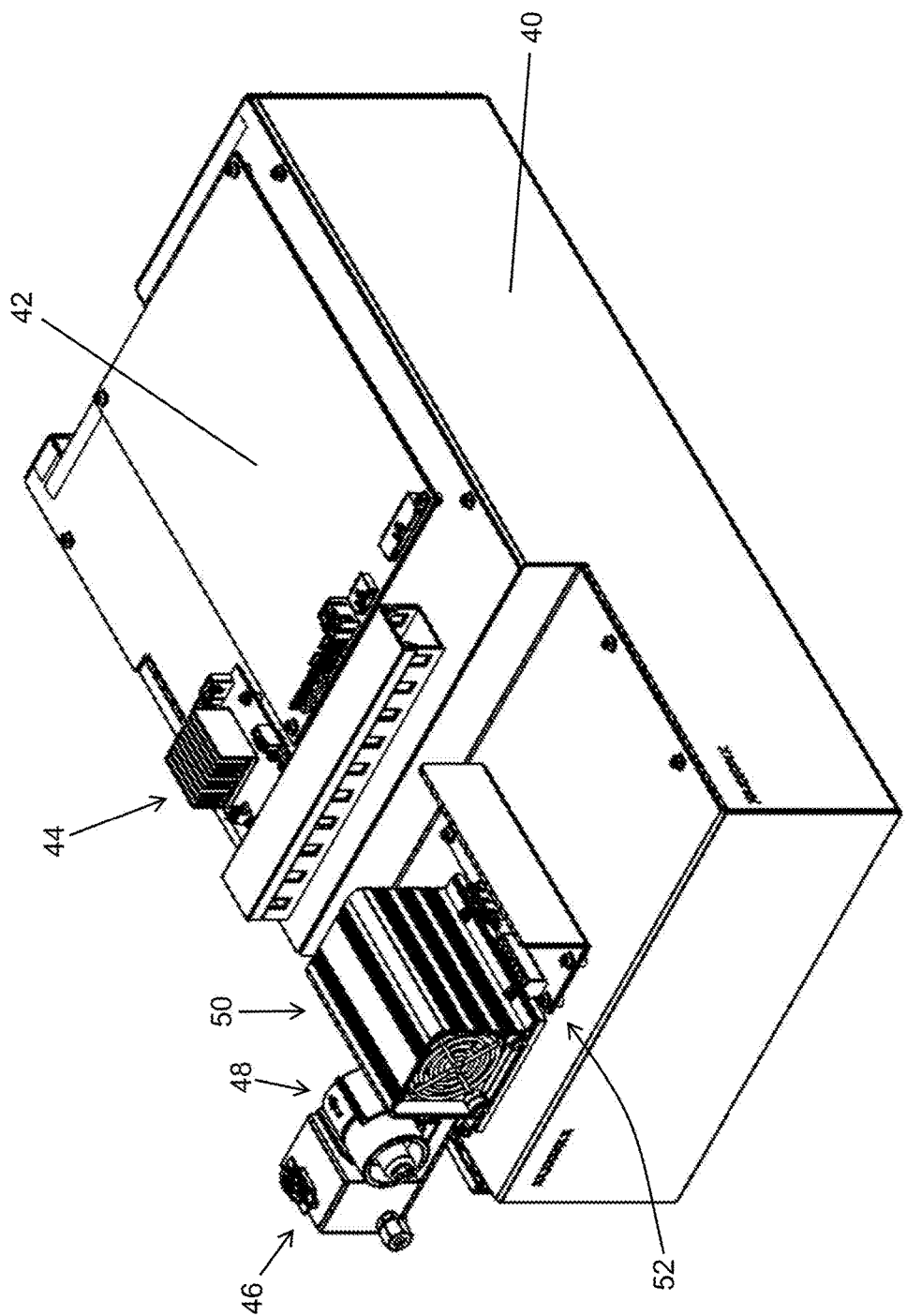
FIG. 2 is a view of a thermal enclosure and other selected components of a gas sensor in accordance with the present teachings.

FIG. 2 illustrates a thermal enclosure 40 that is entirely enclosed within the chassis 12. The thermal enclosure 40 may comprise a box fabricated from, for instance, various sheet-metal panels, that provides a temperature-controlled environment for various light-source components, optical components and gas cell components housed therein. Several temperature sensors may be provided for monitoring various portions of the gas sensor system 10. Several of these temperature sensors may be provided inside the thermal enclosure 40 and may include two or more sensors in or on the gas cell (discussed below) inside the thermal enclosure, at least one sensor for monitoring air temperature within the thermal enclosure, as well as various dedicated sensors on various of the components within the thermal enclosure (discussed in greater detail below). Additionally, one or more temperature sensors may be positioned outside of the thermal enclosure. All such temperature sensors are monitored and, in addition, one (or more) of the sensor outputs are used as feedback signals to the temperature controller module 52 that controls and stabilizes the internal temperature of the thermal enclosure 40. The system also includes various heating (or cooling) devices which respond to signals provided either by the temperature controller module 52 or by various temperature controllers that are dedicated to locally control the temperature of specific components within the thermal enclosure. A heat exchanger module 50, illustrated in greater detail in FIG. 4, comprises one such device for controlling the general air temperature within the thermal enclosure 40.

Generally, keeping these optical core components of the gas sensor at a fixed temperature, independent of fluctuations of the external temperature, helps improve the accuracy and long-term stability of the gas sensor for several reasons. First, if the gas temperature varies, then so do the shapes of the gas absorption lines. Maintaining the gas cell and the sample gas at a constant temperature eliminates temperature-induced lineshape variations, thus ensuring a more accurate and stable fit to the absorption data. Second, keeping the temperature constant reduces problems associated with unintended or inadvertent optical etalons, or optical back reflections within the optical system. Such unintended or inadvertent etalons can result from fortuitous parallelism of optical surfaces—sometimes on widely separated optical components—thereby causing a Fabry-Perotlike sinusoidal interference pattern, as a function of wavelength, of light transmitted through both surfaces. This effect can lead to apparent but fictitious periodic variations in the absorption data and these variations can add to or subtract from the true absorption lines of interest. Since the gas concentration is proportional to the size of the absorption lines, the etalons can lead to an incorrect measurement of gas concentration. Additionally, etalons can shift or vary with temperature. As a result, a time-dependent temperature variation could be incorrectly interpreted as a time-dependent variation in gas concentration. By stabilizing the temperature of the optical elements, temperature-induced drift in the etalons is eliminated, thus resulting in a more accurate, and more stable over time, measurement of gas concentration.

The exterior of the thermal enclosure 40 also may serve as a mounting platform for various other components. For instance, the system illustrated in FIG. 2 includes a printed circuit board 42 which may serve as a switching and signal conditioning board for routing power and signals to and from other various components in the system. Information processing and system control functions may be performed by the separate internal system computer which may be housed in a separate box (not shown) that is disposed adjacent to the thermal enclosure 40 within the chassis. The on-board internal system computer may comprise a main controller board as well as other common computer components. The illustrated system further includes a photodetector temperature controller board 44, a gas vacuum pump or flow controller 46 for causing gas to flow through the gas cell portion of the sensor system at a pre-determined reduced pressure and a gas filter 48 for eliminating particulates from the incoming gas. Various other standard components that do not require a temperature controlled environment may be housed within the chassis 12 but external to or astride the thermal enclosure 40. Such additional components, which are not illustrated for purposes of clarity, may include a power supply module, computer memory devices such as disk drives or ROM-chip memory, computer peripheral boards such as display controllers or external communications boards, electronic cables and interconnections, a gas manifold and various lengths of gas tubing. A heating tape and associated temperature sensor (not shown) may be provided on one or more exterior surfaces of the thermal enclosure 40 so as to control monitor temperature outside of the thermal enclosure.

Figure 3:
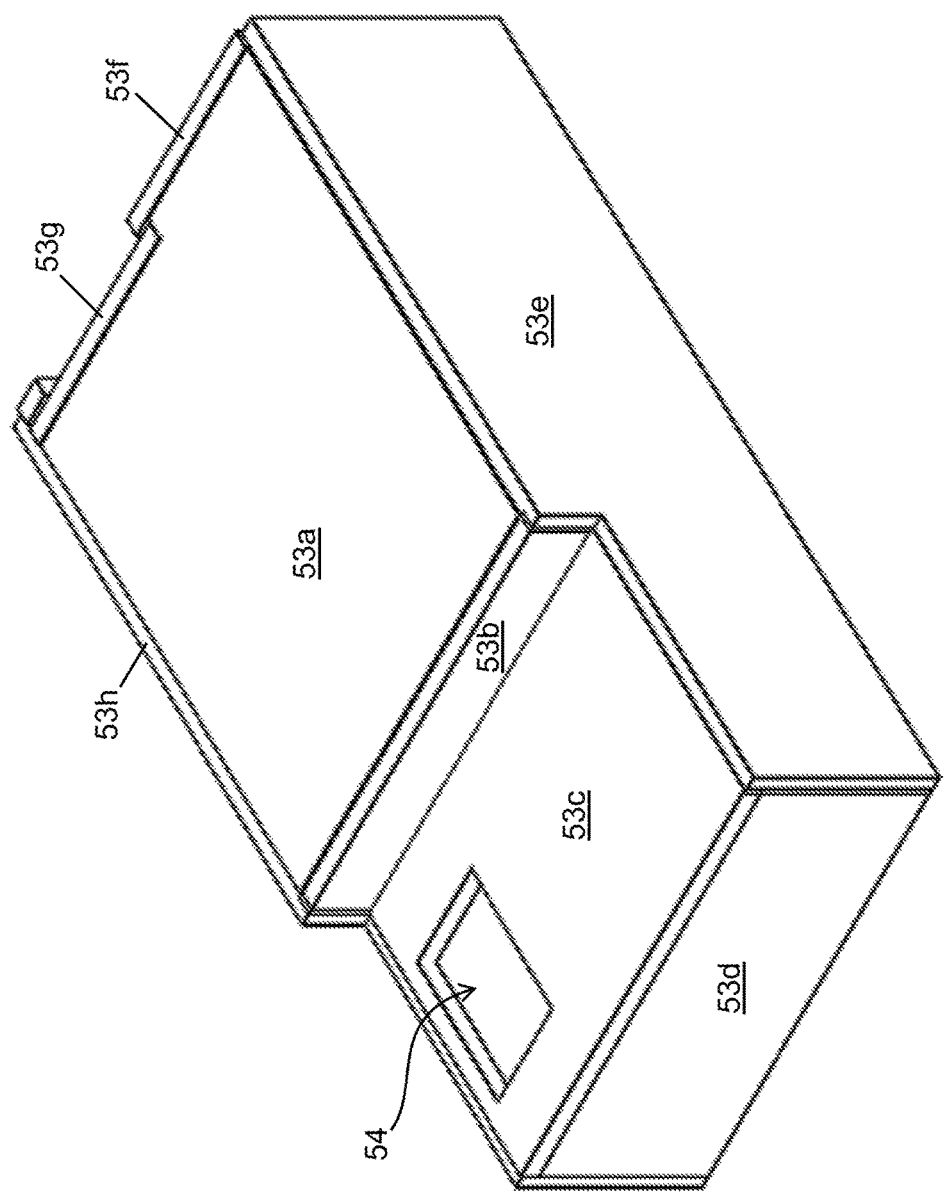
FIG. 3 is a view of thermal insulation material within the thermal enclosure of FIG. 2.

A heat exchanger module 50 that is disposed partly within and partly external to the thermal enclosure 40 is mounted to one portion of the thermal enclosure box. The heat exchanger module 50, which is utilized to control the internal air temperature within the thermal enclosure constant to within ±0.1 Kelvin, is controlled by the temperature controller electronic module 52 which receives internal temperature information from a thermistor or thermocouple attached to an internal surface within the thermal enclosure 40. The tight temperature control within the thermal enclosure is assisted by an insulation material disposed within the thermal enclosure immediately adjacent to the external panels of the thermal enclosure as shown in FIG. 3. The thermal insulation material assists in maintaining the interior of the enclosure thermally isolated from the surroundings. The insulation material may, for example, comprise a synthetic foam material formed into various panels, such as foam panels 53a-53h, that enclose the internal volume within the thermal enclosure at the front, back, top, bottom and sides (note that a bottom foam panel is not visible in FIG. 3). A cutout 54 within a portion of a top portion of the insulation material, together with a mating cutout (not shown) of the thermal enclosure box, enables the heat exchanger 50 to reside partially inside and partially outside of the thermal enclosure. Although not shown, one or more additional cutouts in the thermal enclosure box and insulation may be provided to allow passage of electrical wires and gas-carrying conduits (for instance, by means of electrical feedthroughs or tubing unions attached to the thermal enclosure box) into the thermal enclosure.

Figure 4A:
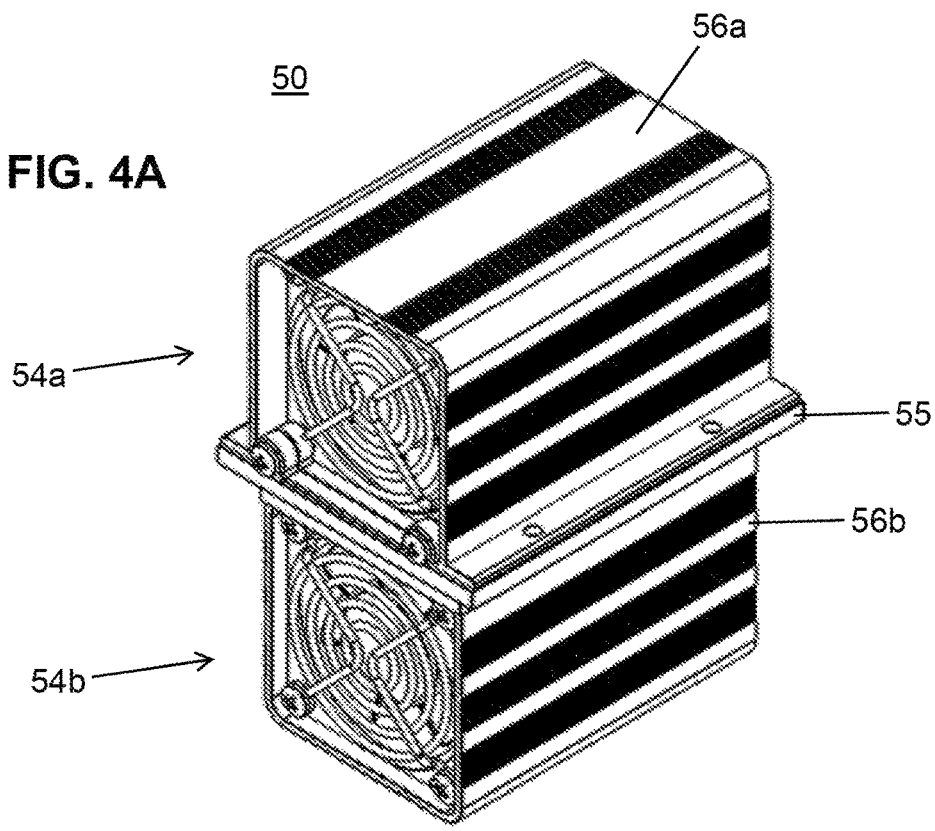
FIG. 4A is a perspective view of a heat exchanger assembly in accordance with the present teachings for controlling and homogenizing temperature within a thermal enclosure.
Figure 4B:
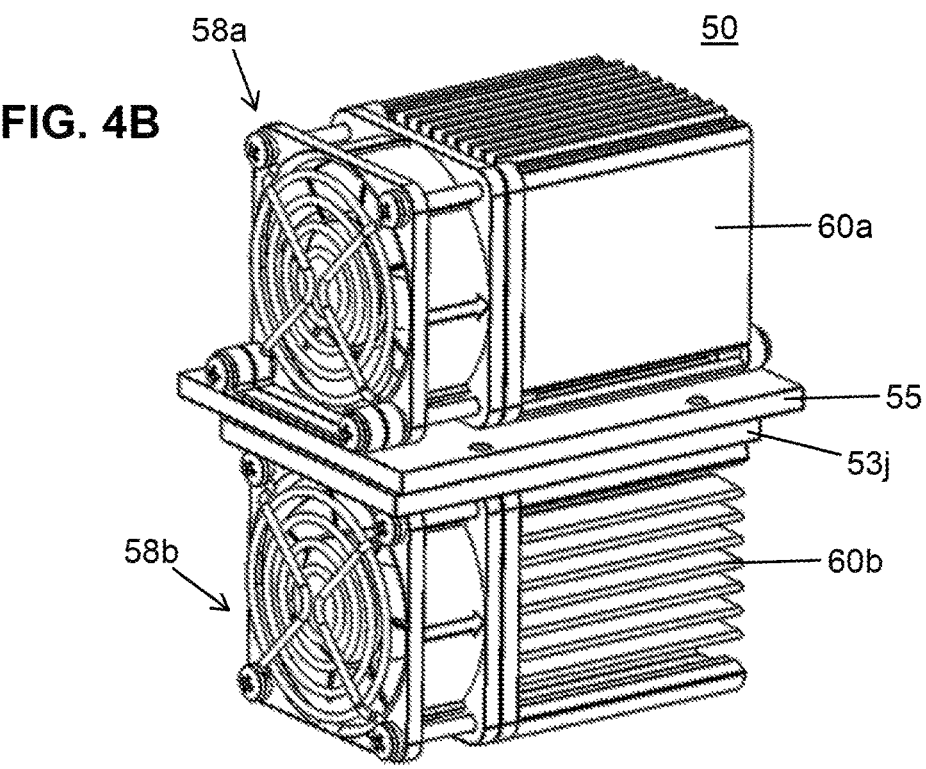
FIG. 4B is another perspective view of the heat exchanger of FIG. 4A with housings removed so as to expose internal components.
Figure 4C:
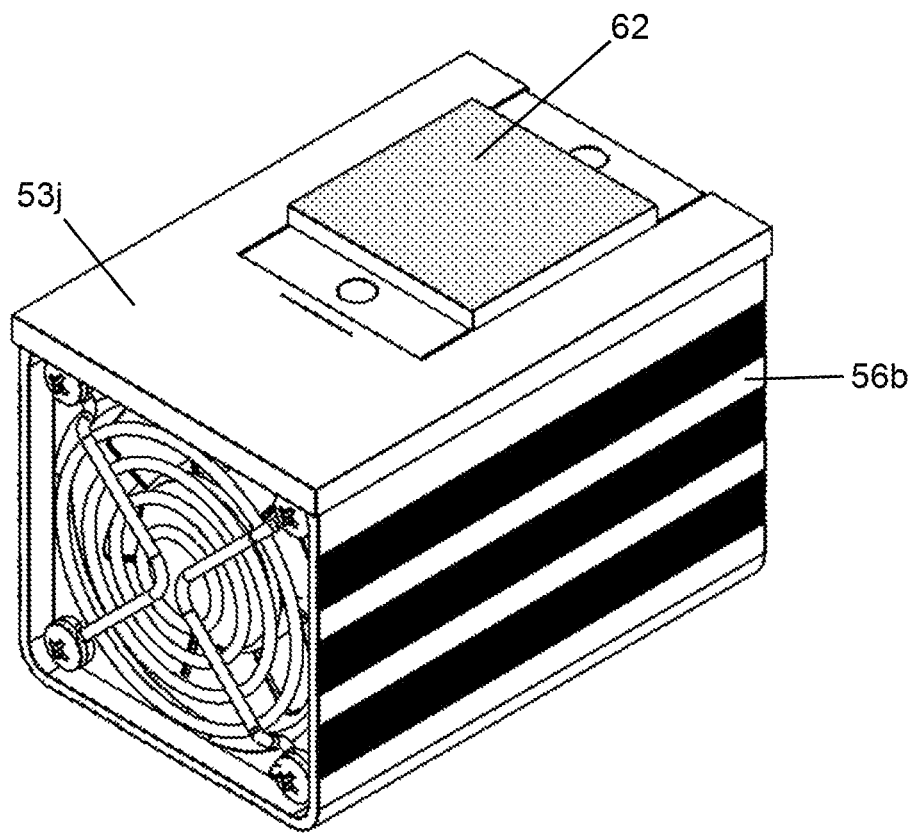
FIG. 4C is another perspective view of the heat exchanger of FIG. 4A with an upper portion removed so as to expose internal components.

FIGS. 4A-4C illustrate various depictions of an exemplary heat exchanger assembly 50, isolated from the remainder of the gas sensor system. FIG. 4A shows that the heat exchanger assembly 50 comprises two separate assemblies, as may be available commercially—a first fan and heat sink assembly 54a that, in operation, is positioned outside of the thermal enclosure and a second possibly identical fan and heat sink assembly 54b that, in operation, is positioned inside of the thermal enclosure. The first and second fan and heat sink assemblies are attached, for instance, by screws or other fasteners, to a mounting plate 55. The mounting plate 55 is itself similarly attached, in the final system, to the thermal enclosure box.

The first fan and heat sink assembly 54a may include a cover 56a that encloses the heat sink portion. Likewise, the second fan and heat sink assembly 54b may include a cover 56b that encloses its heat sink portion. The covers assist in channeling air flow created by operation of the associated fan over the heat sink portion so as to assist in exchange of thermal energy between the respective heat sink and the flowing air. FIG. 4B depicts the same heat exchanger assembly 50 with the covers removed so as to expose the first fan 58a, the first heat sink 60a, the second fan 58b and the second heat sink 60b. FIG. 4B also illustrates an insulation panel 53j disposed between the first 54a and second 54b fan and heat sink assemblies. The insulation panel 53j may be constructed of a suitable insulating material, such as synthetic foam, and serve to partially fill in the cutout portion 54 of the main insulation shown in FIG. 3.

FIG. 4C depicts the same heat exchanger assembly 50 with the entire first fan and heat sink assembly 54a and the mounting plate removed. FIG. 4C illustrates that a thermoelectric cooler (TEC) assembly 62 is maintained in close thermal contact with and between the first and second heat sinks 60a, 60b. For instance, screws or other fasteners may be provided so as to engage both the first and second heat sinks 60a, 60b while passing through clearance holes in mounting flanges of the thermo-electric cooler assembly 62 so as to tightly bind the thermo-electric cooler between the two heat sinks. As is well known, application of an electric current through a thermo-electric cooler causes heat to be pumped from a "cold side" of the thermo-electric cooler to a "hot side" of the thermo-electric cooler. If the "hot side" is exposed to a temperature reservoir that is maintained at ambient temperature than the thermo-electric cooler will serve the purpose of cooling materials that are in thermal contact with its "cold side". However, if the "cold side" is exposed to the ambient temperature thermal reservoir, then the thermo-electric cooler can serve equally well as a heater, causing elevation of temperature above ambient for materials exposed to its "hot side". The positions of the hot and cold sides may be reversed simply by reversing the polarity of the electric current flow through the device.

In an exemplary gas sensor system in accordance with the present invention, the air volume within the thermal enclosure 40 (FIG. 2) is maintained at a constant temperature that is above ambient. The temperature control system may be configured to maintain an operating temperature of the operating environment within a range from about 0° C. to about 70° C. with a temperature deviation of about +1° C. or less. In one example, the operating temperature may be maintained between about 10° C. to about 60° C., between about 20° C. to about 50° C., or between about 30° C. to about 40° C. Exemplary temperature variance windows may include ±1° C., ±0.5° C. or ±0.1° C. of the operating temperature.

In various other typical operating situations, the thermal enclosure temperature is set in the 35-40° C. range, and the temperature is stabilized to within ±0.1° C. of the target temperature. Thus, the thermo-electric cooler 62 (FIG. 4C) is typically operated such that the side facing the interior of the thermal enclosure is the "hot side". The inventors have determined that there are several advantages to having the thermal enclosure's set point temperature elevated above typical room temperature (~20-25° C.). First, the TEC element is more efficient when operating in heating mode rather than cooling mode. Second, keeping the optics at an elevated temperature avoids problems that can occur with water condensation on optical elements within the thermal enclosure (the details of the optics discussed in greater detail, following). Finally, if the enclosure's set-point temperature were to be set close to the ambient temperature, then the TEC element could disadvantageously cycle repetitively between heating and cooling states as it acts to stabilize the enclosure temperature. If the TEC element were allowed to switch between these two operating states, small electrical spikes, changes or other fluctuations could occur, and these spikes or fluctuations could propagate to other elements in the system (e.g., the detector). Since the sensor system is designed to measure very small absorption features very accurately, any electronic fluctuation of this sort could result in a significant change or spike in the measured gas concentration, thus leading to an inaccurate measurement.

Figure 5A:
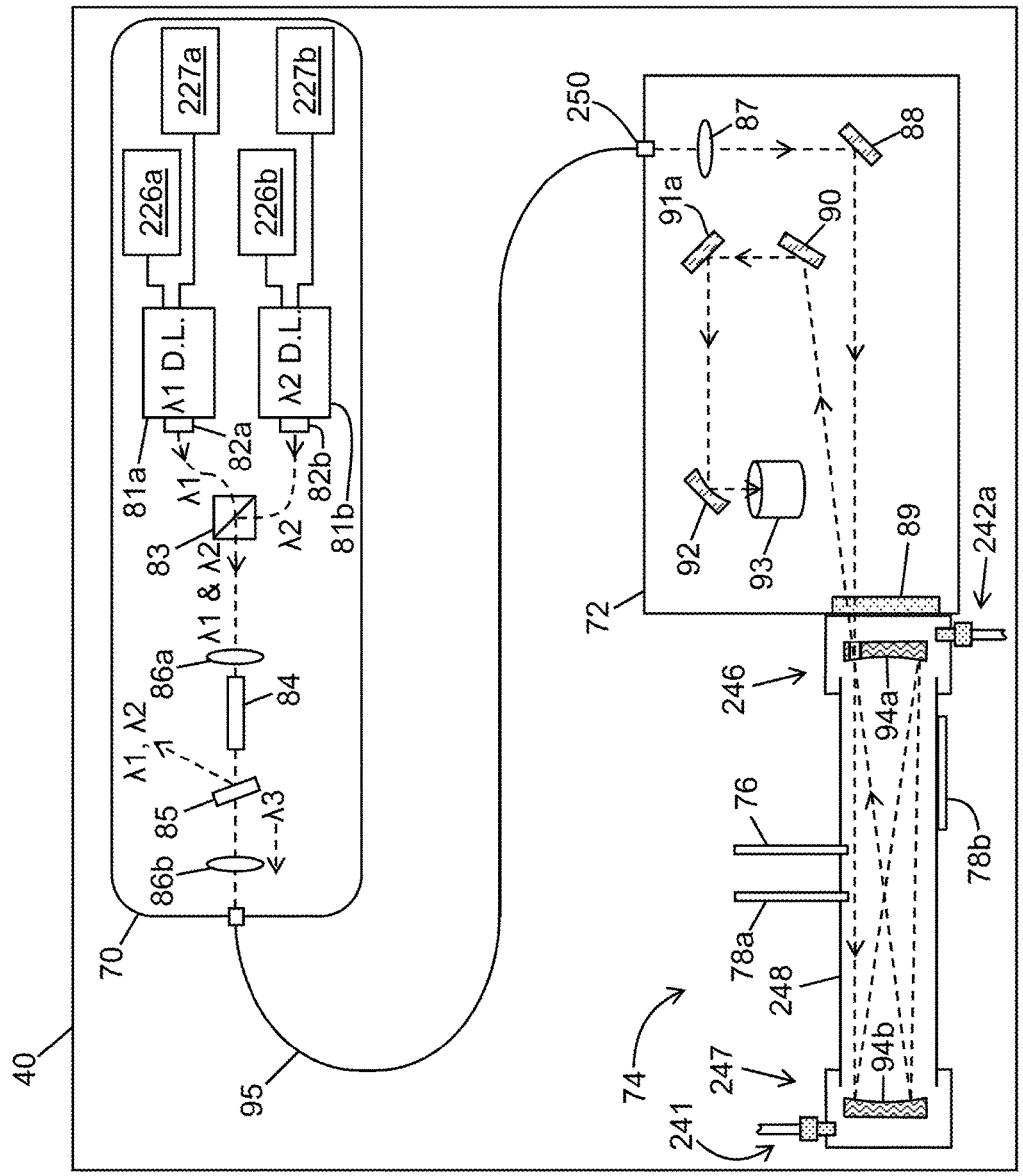
FIG. 5A is a schematic illustration of a first alternative configuration of optical pathways within a gas sensor in accordance with the present teachings.
Figure 5B:
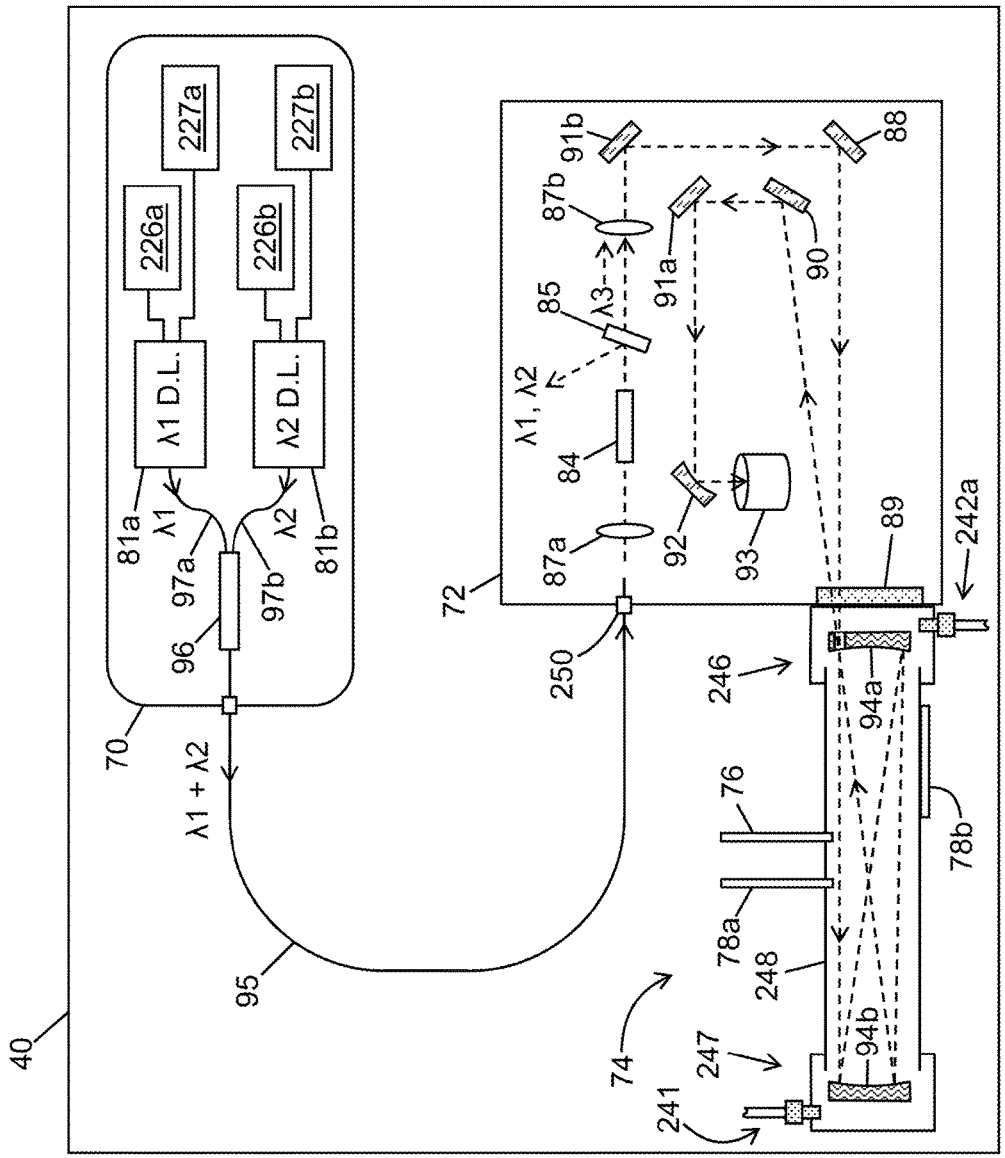
FIG. 5B is a schematic illustration of a second alternative configuration of optical pathways within a gas sensor in accordance with the present teachings.
Figure 5C:
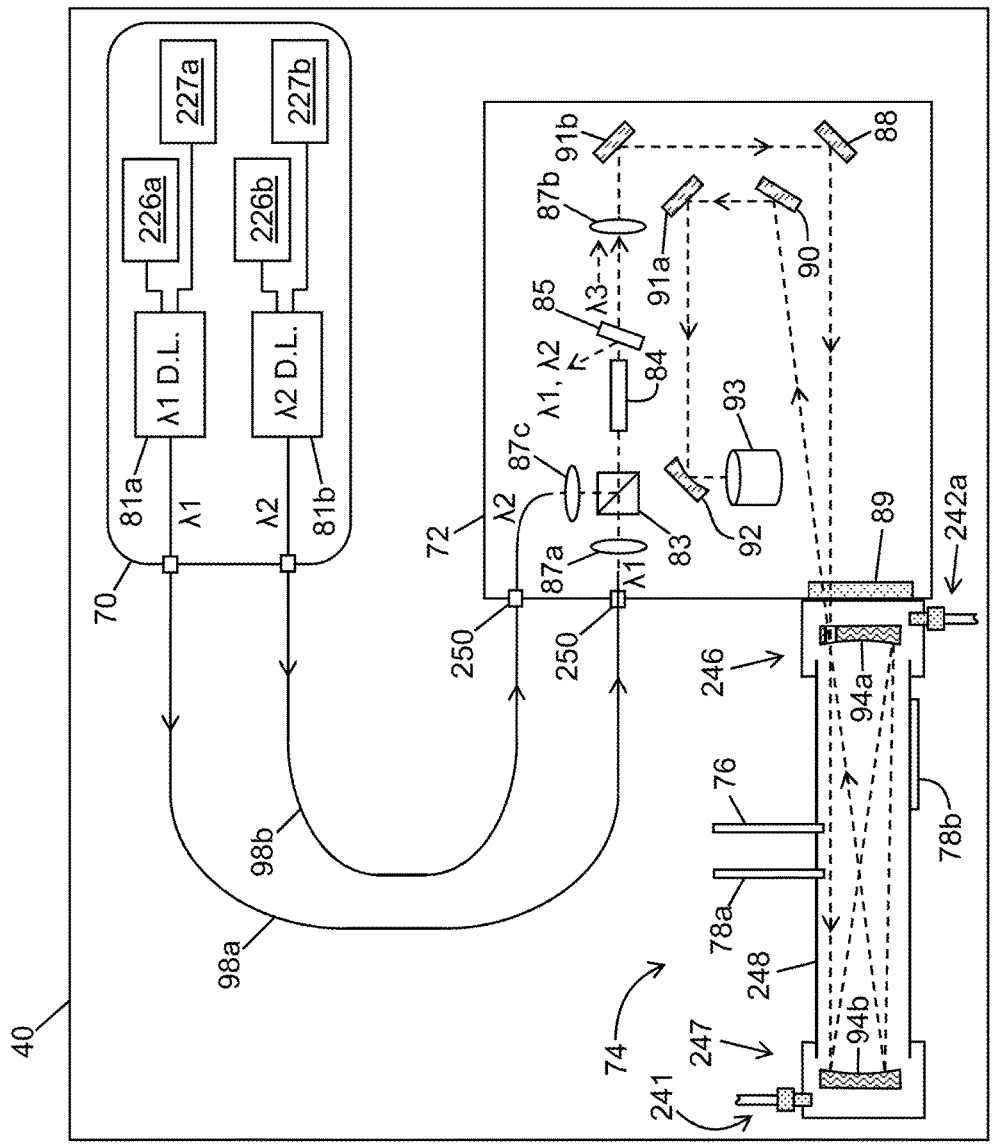
FIG. 5C is a schematic illustration of a third alternative configuration of optical pathways within a gas sensor in accordance with the present teachings.

FIGS. 5A-5C schematically illustrate three examples of alternative optical configurations for a gas sensor system in accordance with the present teachings. These illustrative drawings are not to be construed as limiting in any way, as various features shown in the three exemplary embodiments may be combined or omitted so as to yield other embodiments in accordance with the present teachings. For example, possible embodiments may include various combinations, hybrids or otherwise modified versions—either lacking certain components or having additional components—of the examples illustrated in FIGS. 5A-5B. Each of the embodiments shown in FIG. 5 generally illustrates a laser chamber module 70, an optical chamber module 72 and a gas cell 74. This set of three modules is generally completely enclosed within the temperature controlled volume enclosed by the insulation material (FIG. 3).

The laser chamber module 70 produces an output light emission that, preferably, is directed into the optical chamber module 72 by means of at least one optical fiber or optical fiber cable (fiber or cable 95 in FIGS. 5A-5B and fibers or cables 98a-98b in FIG. 5C). In various embodiments, the laser chamber module 70 produces as an output a coherent narrow-bandwidth mid-IR light emission whose wavelength is tunable across one or more rovibrational bands of a target gas. In various other embodiments, the laser chamber module produces two multiplexed light emissions in the near-IR or short-wavelength IR, the wavelengths of which are configured such that a mid-IR light may be generated within an optically non-linear crystal within the optical chamber module such that the wavelength of the generated mid-IR light is tunable across one or more rovibrational bands of a target gas.

The optical chamber module 72 receives the light emission from the laser chamber module 70, performs any required conditioning or filtering of the received light, directs the received light into the gas cell 74 in which it is reflected a plurality of times, receives the reflected light from the gas cell and directs it to a photo-detector. At least one fiber optic feed-through 250 serves to guide the optical fiber or fiber-optic cable (fiber or cable 95 in FIGS. 5A-5B and fibers or cables 98a-98b in FIG. 5C) into the optical chamber module. The optical fiber or cable delivers laser light from the laser chamber module into the optical chamber module. In the embodiment illustrated in FIG. 5A, the laser light is mid-IR light comprising wavelength λ3 and, thus, in that embodiment, the fiber is preferably a specialty fiber that has adequate mid-IR transmission characteristics, such as a chalcogenide glass fiber. In the embodiments shown in FIGS. 5B-5C, the delivered laser light is a multiplexed light comprising two wavelengths, λ1 and λ2, which are focused into a non-linear crystal 84 within the optical chamber module 72 so as to generate a mid-IR light of a third wavelength, λ3. Other components within the optical chamber module 72 may include one or more turning mirrors 91a, 91b, a steering mirror 88, a pick-off mirror 90, a focusing concave mirror 92 and a light detector 93. Each of the mirrors and the detector may be associated with appropriate mounting and positioning hardware so as to align each respective component and maintain the component in its aligned position and orientation. Light ray paths within the optical chamber module are denoted by dashed lines with arrows.

The detector 93 may comprise a photodiode, such as one based on indium arsenide (InAs), indium antimonide (InSb) or mercury cadmium telluride (MCT) that has an electronic response (either as a photocurrent or a voltage) that is sensitive to mid-infrared radiation. Since the performance of such detectors improves at low temperatures, the detector may be provided as a commercially available package that includes an internal thermo-electric cooler and an internal temperature sensor, such as a thermistor. The package may also include a signal amplifier. In one example, an MCT detector generates a current from the mid-IR light, and this photocurrent is fed into a transimpedance amplifier that converts current into a proportional voltage. The voltage may be digitized at various discrete time points—for example, 1024 points. FIG. 11B (discussed in greater detail below) provides an example of such a proportional voltage plotted against time.

Electrical leads or pins may also be included in or on the detector package for application of a bias (or reverse bias) voltage and for measurement of a signal voltage or current. The package may also include a window for protection of the photosensitive element. The electrical leads and connections to the detector may be provided by internal wires or cables (not shown) that are electrically coupled to a multi-pin electrical connector (not shown). A separate electrical feed-through (not shown) and associated wires (not shown) may be used to provide electrical connections to a thermo-electric cooler and temperature sensor supported on the crystal, filter and lens assembly.

The gas cell 74 receives a flowing sample (or other) gas at controlled reduced pressure and controlled temperature through a gas inlet port (not shown in FIG. 5), directs the flowing reduced-pressure gas through a gas-cell volume such that the light received from the optical chamber is caused to pass through the gas in the gas-cell volume a plurality of times and exhausts the gas through a gas outlet port (not shown in FIG. 5). The pressure and temperature within the gas cell may be measured by a pressure transducer 76 and at least a first gas-cell temperature sensor 78a (such as a thermocouple or thermistor, both of which have access to the interior of the gas cell by means of side ports. A second temperature sensor 78b may be mounted against an external surface of a tube portion 248 of the gas cell. The pressure transducer sends a signal to a controller or software component or module for the purpose of monitoring and controlling the sample gas pressure within the gas cell 74. The gas cell may be operated such that the pressure of a sample gas therein is maintained at a reduced pressure (50-300 Torr)—typically 200 Torr.

The gas cell 74 may comprise any type of gas sampling cell capable of directing a mid-infrared beam along a pre-scribed path through a gas but is preferably a Herriott cell in which the light is reflected two or more times between a pair of concave mirrors 94a, 94b facing one another at opposite ends of a tube or pipe 74 through which the gas flows. The mirror 94a nearest the optical chamber module 72 has a small hole—or possibly a small surface portion lacking a mirror coating—that permits the un-attenuated beam to enter the gas cell from the optical chamber module and that permits the attenuated beam to return to the optical chamber module. The number of reflections through the gas cell may be controlled by adjustment of the position and orientation of the steering mirror 88. Preferably, the number of reflections through the gas cell is determined in conjunction with consideration of the specific absorbance of the target infrared absorption line(s) such that the optical power of the attenuated beam reaching the detector is within a linear and relatively noise-free response regime of the detector.

As shown in FIG. 5, the gas cell 74 may comprise a Herriott cell that includes a tube 248 onto which is attached a front end assembly 246 and a back end assembly 247. The back end assembly 247 of the gas cell 74 may receive an input flow of the sample gas through a gas inlet port 241 and also houses the rear mirror 94b. The front end assembly 246 may include a mounting bracket for attaching the gas cell 74 to the optical chamber module 72 and may exhaust the sample gas, in some embodiments (e.g., see FIG. 10A), through a gas outlet port 242a. In various other embodiments (e.g., see FIG. 10B), the gas outlet port 242a may plugged and the front end assembly may exhaust the sample gas directly into the optical chamber module 72. The front end assembly 246 may also house the internal front mirror 94a that enables laser light from the optical chamber module to pass into the gas cell, reflects the light from the tube 248 back into the tube at least one time and that permits the attenuated light to return to the optical chamber module 72.

In the first exemplary system configuration, which is illustrated in FIG. 5A, the laser chamber module 70 comprises two laser light sources 81a, 81b producing laser light emissions at wavelengths $\lambda 1$ and $\lambda 2$, respectively. Preferably, the laser light sources comprise laser diodes. In the case that the first laser 81a comprises a laser diode, then this first laser is electrically coupled to both a first laser diode current driver module 226a and a first thermoelectric cooler driver module 227a. Likewise, in the case that the second laser 81a comprises a laser diode, then this second laser is electrically coupled to both a second laser diode current driver module 226b and a second thermoelectric cooler driver module 227b. Each of the thermoelectric cooler driver modules 227a, 227b functions to monitor a temperature sensor inside the package of the associated laser diode, and to drive current to a thermoelectric cooler inside the package to stabilize the laser diode temperature. The laser light emissions, which may pass through short lengths of fiber pigtails, are launched into collimated free space beams by collimating lenses 82a and 82b. These two beams are combined by beam combiner (multiplexer) 83 so as to overlap both in space and in the orientation of their electric vectors. The multiplexer 83 may be a reflection/transmission-based wavelength multiplexer in which one laser source is transmitted through a dichroic filter while the other laser source is reflected by the filter. The laser sources and filter are oriented so that at the output port of the multiplexer the two laser sources are combined into a single beam.

The two laser sources, now combined into a single beam, are next coupled into the nonlinear crystal 84 by lens 86a. The non-linear crystal is of a type such that a co-propagating light of a third wavelength, $\lambda 3$, is generated within the crystal by interaction of the electric fields of the two laser emissions with the crystal. The nonlinear optical crystal 84 may be periodically poled, and configured to frequency-convert the first and second laser beams. For example, the periodically-poled nonlinear optical crystal 84 may achieve phase or quasi-phase matching of fundamental frequency photons and corresponding difference frequency photons through artificially structuring the material domains. The periodically-poled nonlinear optical crystal 84 may include any of a variety of crystalline materials, such as, for example, Potassium Titanyl Phosphate (KTP), Lithium Niobate (LN), Lithium Tantalate (LT), and III-V materials. According to one embodiment, the nonlinear optical crystal 84 is a periodically poled lithium niobate (PPLN) structure having a length in the range of about 10 to about 60 mm.

The two laser light sources 81a, 81b and the non-linear crystal 84 are configured and operated such that the wavelength $\lambda 3$ coincides with a mid-IR spectral absorption feature of a target gas—for instance, a strong absorption line in the vibrational spectrum of a specific chemical species that is targeted by the gas sensor. As discussed further below, the wavelength $\lambda 3$ may be tuned so as to periodically sweep across a target absorption line by tuning, in some embodiments, only one of the source laser wavelengths—either $\lambda 1$ or $\lambda 2$. In such a case, a preferred orientation for the multiplexer 83 is for the tuned wavelength—either $\lambda 1$ or $\lambda 2$—to be reflected by the filter of the multiplexer and the non-tuned laser source to be transmitted through the filter. This orientation minimizes etalon effects which can cause distortions in the absorption signal and lead to inaccuracies in the measured gas concentration value.

After passing through the nonlinear crystal, the residual light from the two laser sources is removed from the mid-infrared beam with an absorptive and/or reflective optical filter 85. The filter 85 may comprise an optical bandpass or edge filter 85 that transmits the light of wavelength $\lambda 3$ while rejecting the light of wavelength $\lambda 1$ and the light of wavelength $\lambda 2$. In some embodiments, the filter 85 may be a piece of polished germanium (with or without a dielectric coating to enhance the reflectivity of $\lambda 1$ and $\lambda 2$), or a transmissive optical substrate with a dielectric coating on one or both surfaces to reflect the two laser source wavelengths and transmit the wavelength $\lambda 3$. The filter 85 may also be wedged to further reduce optical fringing between the input optical face and output optical face of the filter. For example, the wedge may be from about 3° to about 5°. In the configuration shown in FIG. 5A, the output of the laser chamber module 70 is the light comprising the wavelength $\lambda 3$ which is delivered to the optical chamber 72 by means of an optical fiber (or optical fiber cable) 95. In this particular example, the optical fiber 95 may be either single mode or multi-mode. The design shown in FIG. 5A has an advantageous property that the laser chamber module is fully interchangeable in the sense that the gas sensor can be physically configured for use with a different target gas by simple replacement of this module.

Still referring to FIG. 5A, the λ3-wavelength light is launched into an optical fiber 95 by lens 86b and delivered by the optical fiber 95 into the interior of the optical chamber module 72 where it is launched into a free-space collimated beam by means of collimating lens 87. The steering mirror 88 directs the light at a suitable position and angle through a mid-IR transparent window 89 and into the gas cell 74 where the light is partially attenuated by optical absorption of a portion of the light by a sample (or calibration) gas flowing through the gas cell 74. The attenuated λ3-wavelength light returns to the optical chamber module 72 through the window 89 along a path that is slightly offset from the path of the outgoing beam (the outgoing beam is the beam traversing from the steering mirror to the window). The slightly offset attenuated beam is further separated from the path of the outgoing beam by the pick-off mirror 90. After possible additional reflection by a turning mirror 91a, the returning attenuated beam is focused by the concave mirror 92 onto a photo-detector 93. The photo-detector may be any suitable detector capable of responding to mid-IR light, such as a well-known mercury-cadmium-telluride (MCT) detector.

The second exemplary system configuration illustrated in FIG. 5B differs from that shown in FIG. 5A in that the non-linear crystal 84 and, necessarily, the optical bandpass or edge filter 85 are moved from the laser chamber module 70 into the optical chamber module 72. This configuration eliminates any requirement for a free-space beam propagation region within the laser chamber module and thus the laser light of wavelength λ1 emitted from laser 81a and the laser light of wavelength λ2 emitted from laser 81b can be transmitted to a fiber-optic combiner or multiplexer 96 by short lengths of fiber "pigtails" 97a, 97b. The fiber optic combiner or multiplexer 96, which may be similar to a wavelength division multiplexer used in telecommunication systems, multiplexes the light of both wavelengths into the fiber optic cable 95 for delivery to the optical chamber module 72. In this example configuration, it is desirable that the optic combiner or multiplexer 96 combines the beams with parallel polarizations and the fiber pigtails 97a, 97b and fiber optic cable 95 all comprise single-mode polarization-maintaining fiber, since the two laser lights must be similarly polarized upon entry into the non-linear crystal 84. Although the collimating lenses 87a is illustrated as a discrete element located external to the end of the fiber 95, it may alternatively comprise a lens incorporated into an assembly at the end of the fiber, such that the fiber and lens are integrated together as a single unit.

The third exemplary system configuration illustrated in FIG. 5C differs from that shown in FIG. 5B in that the two laser emissions, comprising wavelength λ1 and wavelength λ2, are not combined at all in the laser chamber module 70 but are instead launched into separate respective single-mode polarization-maintaining fibers 98a, 98b. These two fibers deliver the separate laser emissions into the optical chamber module 72 which are then converted to collimated free space beams by collimating lens 87a and collimating lens 87b, respectively. These two beams are caused to overlap in space on a path towards the non-linear crystal 84 by beam combiner 83. The two fibers 98a, 98b should be oriented so that the polarizations of the separate laser emissions are parallel to one another after being combined by the beam combiner 83 and during passage through the non-linear crystal 84. Although each of the collimating lenses 87a, 87b is illustrated as a discrete element located external to the end of its associated fiber, either or both of these lenses may alternatively comprise a lens incorporated into an assembly at the end of the associated fiber, such that the fiber and lens are integrated together as a single unit.

The system configuration illustrated in FIG. 5C has the advantage that the core diameter of each of the optical fibers 98a, 98b may be optimized for the mode size of the respective wavelength propagating through it. This allows the light emission of each wavelength—wavelength λ1 and wavelength λ2—to propagate through its respective fiber without significant disruption caused by attenuation within the fiber or stimulation of secondary modes within the fiber. It provides a further potential advantage in that there is no requirement for free-space propagation of light of wavelength λ3 within the laser chamber module 70.

The properties and features of the light source used in the gas sensor are now discussed. Gas sensors in accordance with the present teachings may employ a difference-frequency-generation (DFG) device in which mid-infrared light is generated by combining two laser sources in a nonlinear crystal such as periodically-poled lithium niobate (PPLN) crystal. In a well-known fashion, coherent light at the difference frequency between the two input laser frequencies is generated in the nonlinear crystal. The equation describing this process is:

$$f_3 = f_1 - f_2, \quad \text{Eq. 2}$$

in which $f_1$=input laser frequency #1, $f_2$=input laser frequency #2, and $f_3$ is the DFG output frequency. Equivalently, in terms of the laser wavelength:

$$\frac{1}{\lambda_3} = \frac{1}{\lambda_1} - \frac{1}{\lambda_2} \quad \text{Eq. 3a}$$

in which $\lambda_1$ and $\lambda_2$ are the two input laser wavelengths, and $\lambda_3$ is the DFG output wavelength. This can be rearranged to $$\lambda_3 = \frac{(\lambda_1 \lambda_2)}{(\lambda_2 - \lambda_1)}. \quad \text{Eq. 3b}$$

For example, for methane detection, the two source laser wavelengths are approximately 1053 nm and 1554 nm which, via difference-frequency generation, produce mid-infrared light at around 3.27 microns.

The two laser sources can be diode lasers which have the advantage of being compact, highly efficient, direct emitters that can be frequency-tuned via temperature and current. Diode lasers have several additional characteristics which provide advantages when used in gas sensors in accordance with the present teachings. Firstly, diode lasers may be readily obtained in standard packages that include an integrated optical isolator and an integrated polarization-maintaining (PM) optical fiber (a so-called "pigtail") as an output. Having an optical isolator positioned close to the output facet of the diode laser emitter as provided in various standard packages helps to keep the diode laser's output intensity and frequency stable and resistant to disruption from optical back reflections coming from downstream optical surfaces. The integrated PM fiber pigtail is useful for easy coupling to downstream optical components, especially in those embodiments which require polarization preservation. Secondly, many readily available laser packages include a wavelength selection element (e.g., volume holographic grating, aka volume Bragg grating) positioned close to the diode laser emitter to stabilize and narrow the laser's output wavelength. Alternately, the diode laser can be provided as a distributed-feedback (DFB) laser diode in which the device has a built-in periodic structure that acts to stabilize and narrow the laser's output wavelength. Alternatively, the diode laser can be a distributed-Bragg-reflector (DBR) laser diode, which consists of a laser diode that is sandwiched between two Bragg reflector structures—in this case, the Bragg structures also act to stabilize and narrow the laser's output wavelength. Yet a third advantage is that the emission wavelength of a diode laser can easily be tuned, within limits, by either temperature or current control.

Because of the above-listed advantages, the use of diode lasers can enable the difference-frequency generation of tunable mid-IR light having a very narrow-linewidth (typically 2 MHz) within a typical mid-infrared wavelength range of 3.0-4.8 microns. As discussed further below, tuning of the mid-IR laser source may be achieved by tuning one of the source laser wavelengths. The wavelength region of 3.0-4.8 microns is attractive for gas sensing measurements because the absorption strengths of the gases of interest are very strong in the mid-IR—on the order of 10 to 10,000 times larger than in the near-infrared region (~1-2 microns). The coherent mid-IR light generated as described above may be characterized by a narrow line width of less than about 10 MHz. In specific embodiments, the line width of the coherent beam output may be less than about 2-3 MHz or, alternatively, less than about 1 MHz. The line width of the coherent beam is given as the width, e.g., the full width at half-maximum (FWHM) of the optical spectrum in terms of frequency. However, as appreciated by a person having ordinary skill in the art, the line width for the coherent beam may alternatively be expressed in terms of wavenumber or wavelength. Some other characteristics of the difference-frequency generated mid-IR light are: rapid tunability over a frequency range of around 30-60 GHz (or equivalently, about 1-2 wavenumbers) and operating wavelength in the 3.0-4.8 μm (micron) range.

The mid-infrared light generated with the difference-frequency technique can be tuned in wavelength by changing the temperature set-point of the DFB or DBR laser diode. Changing the laser diode temperature causes its output wavelength to shift, which in turn produces a corresponding shift in the mid-IR laser wavelength. This temperature-tuning of the laser diode wavelength allows the mid-IR laser wavelength to be fine-tuned to the exact wavelength needed to measure the absorption lines of interest. The laser diode temperature is monitored and controlled by a thermistor temperature sensor located near the laser diode chip and a thermoelectric cooler (TEC) element on which the laser diode chip is mounted.

Additionally, the mid-IR laser wavelength can be rapidly tuned by applying a current modulation to only one of the two source diode lasers. The laser to which the current modulation is applied may be referred to as a "scanning laser". The other laser may comprise and may be referred to as a wavelength-stabilized laser. Modulating a diode laser's drive current produces a corresponding modulation of the laser's output wavelength, which, as above, modulates the mid-infrared laser source's wavelength. This type of wavelength tuning is fairly high-bandwidth, resulting in a laser source that can scan through absorption lines at high frequency. The typical tuning range of the mid-infrared light resulting from this current modulation of one of the source lasers is approximately 50 GHz.

Figure 6:
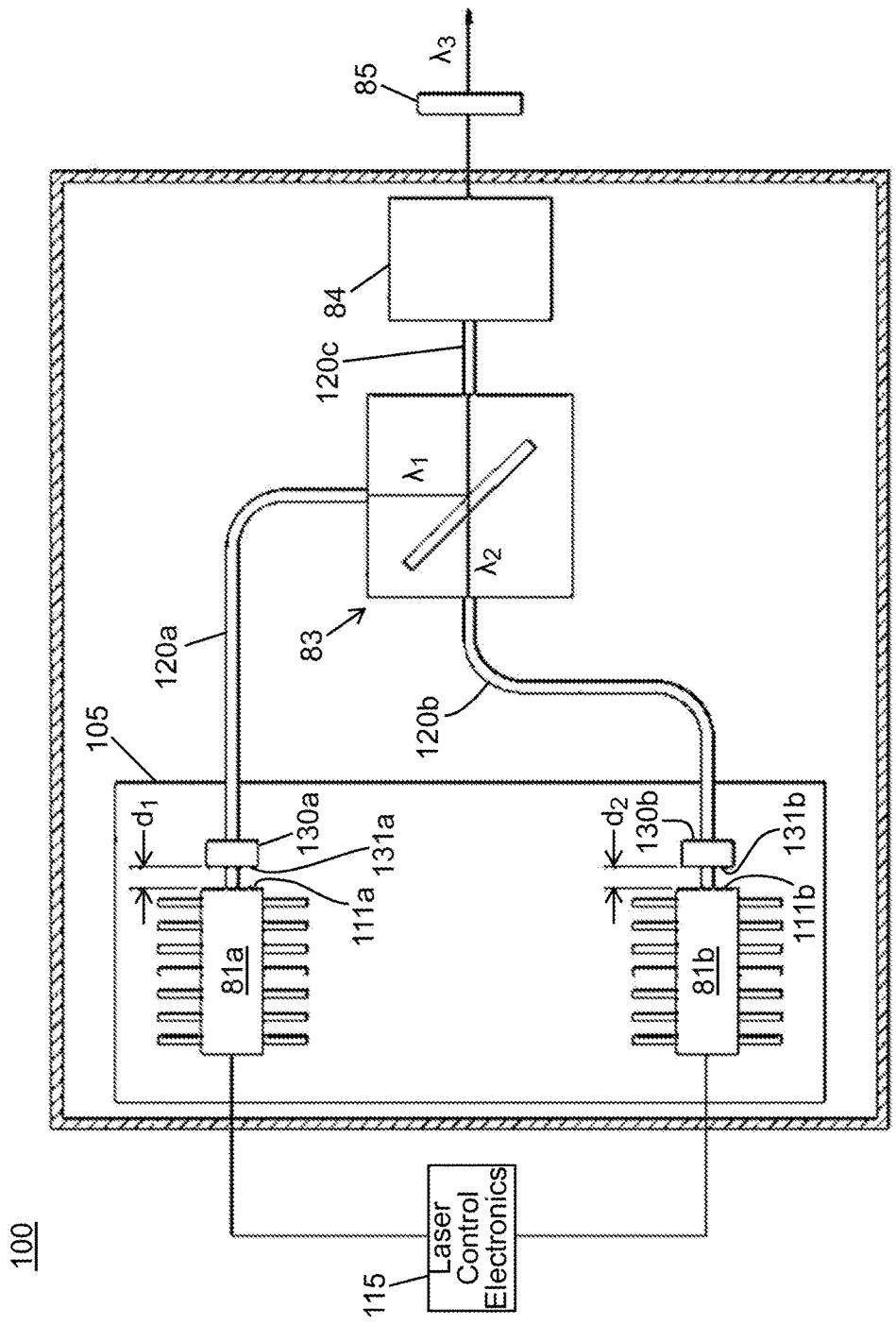
FIG. 6 is a detailed schematic illustration of a laser light source for generating mid-infrared light according to various embodiments in accordance with the present teachings.

FIG. 6 a detailed illustration of another light source for a gas sensor in accordance with the present teachings. With reference to FIG. 6, a laser light source 100 is provided for generating mid-infrared radiation or light characterized by a wavelength λ3 in a range of about 4 μm to about 5 μm. The laser light source 100 includes a first laser 81a, a first optical isolator 130a, a second laser 81b, a second optical isolator 130b, a multiplexer 83, a nonlinear optical crystal 84 optically coupled by the multiplexer 83 with the first and second optical isolators 130a, 130b, and a filter 85 downstream along the optical path from the nonlinear optical crystal 84. The first laser 81a may be configured to generate a first laser beam having a wavelength λ1 in a range of about 1500 nm to about 1650 nm and is optically coupled to a first optical isolator 130a, which is subsequently optically coupled to the multiplexer 83. In the represented embodiment, the first laser 81a, the first optical isolator 130a, and the multiplexer 83 are optically coupled by optical fiber 120a. The second laser 81b may be configured to generate a second laser beam having a wavelength λ2 in a range of about 1120 nm to about 1200 nm and is optically coupled to a second optical isolator 130b, which is subsequently optically coupled to the multiplexer 83. In the represented embodiment, the second laser 81b, the second optical isolator 130b, and the multiplexer 83 are optically coupled by optical fiber 120b. The multiplexer 83 is configured to combine the first and second laser beams to provide a multiplexer output of combined radiation directed along a common optical path. For example, the multiplexer output directed along the common optical path may be provided by configuring the multiplexer 83 to reflect the first laser beam at wavelength λ1 and to transmit the second laser beam at wavelength λ2. The multiplexer 83 is optically coupled to the nonlinear optical crystal 84 by a single optical fiber 120c, which may further include a focusing element (not shown). The nonlinear optical crystal 84 inputs the multiplexer output directed along the common optical path for the first and second laser beams and outputs a coherent beam that includes a primary or principle component at a wavelength λ3 in a range of about 4 μm to about 5 μm. The coherent beam is subsequently passed through the filter 85 to remove the portions of the light at the original wavelengths λ1, λ2 and output the portion of the coherent beam characterized by the wavelength λ3.

The first laser 81a of the laser light source 100 may be a distributed feedback (DFB) laser having a laser gain medium periodically structured as a diffraction grating. The periodic structure of the gain medium in a DFB laser builds a one dimensional interference grating (Bragg scattering), which provides optical feedback for controlling the first laser 81a. The DFB laser may have an antireflection coating on one end of the cavity and a high reflectivity coating on the opposite end of the cavity. Alternatively, the DFB laser may be a phase-shifted DFB laser having both ends covered by antireflection coatings and with a phase shift in the cavity, such as a single quarter-wave shift at the center of the cavity, or multiple smaller shifts distributed in the cavity.

In one embodiment, the first laser 81a may be a diode laser having an active medium composed of a semiconductor material doped as a p-n junction. In another embodiment, the first laser 81a may be an optical fiber laser (OFL) in which the gain medium is an optical fiber doped with rare-earth elements such as erbium, ytterbium, neodymium, dysprosium, praseodymium, and thulium.

According to an embodiment of the invention, the first laser 81a may be configured to generate a first laser beam having a wavelength λ1 in a range of about 1500 nm to about 1650 nm. In more specific embodiments, the first laser 81*a* may be configured to generate radiation (i.e., lase) at a wavelength λ1 in a range of about 1500 nm to about 1600 nm; at a wavelength λ1 in a range of about 1550 nm to about 1650 nm; at a wavelength λ1 in a range of about 1550 nm to about 1600 nm; and/or at a wavelength λ1 of about 1550 nm.

In an embodiment, the second laser 81*b* of the laser light source 100 may be a quantum-dot type semiconductor laser. A quantum dot laser is a variety of semiconductor laser that incorporates a layer of quantum dots as the active gain medium in its light emitting region. Due to the tight confinement of charge carriers in three dimensions, quantum dots exhibit an electronic structure similar to atoms where the energy levels can be adjusted by controlling the quantum dot dimensions or the quantum dot material composition.

An exemplary quantum-dot laser may be a sub-watt level, highly strained InGaAs/GaAs with a free lasing wavelength of around 1170 nm, but that is capable of being tuned in a wavelength range from about 1147 nm to about 1197 nm. The quantum dot-laser may further include an external cavity holographic grating that serves to stabilize the laser wavelength and narrow the output to single mode operation.

According to an embodiment of the present invention, the second laser 81*b* may be configured to generate a second laser beam having a wavelength λ2 in a range of about 1120 nm to about 1200 nm. In more specific embodiments, the second laser 81*b* may be configured to generate radiation (i.e., lase) at a wavelength λ2 in a range of about 1120 nm to about 1180 nm; at a wavelength λ2 in a range of about 1150 nm to about 1200 nm; at a wavelength λ2 in a range of about 1150 nm to about 1180 nm; and/or at a wavelength λ2 of about 1170 nm.

According to embodiments of the present teachings, the first laser 81*a* and/or the second laser 81*b* of the laser light source 100 may be tunable in that the wavelength of operation can be altered or adjusted in a controlled manner over a range of possible wavelengths. The tunability of the laser 81*a* and/or laser 81*b* may be achieved by a single line, narrow line, or multi-band tuning. According to one embodiment, the first laser 81*a* may be tunable, while the second laser 81*b* further includes an external wavelength selection element in an external cavity configuration. According to another embodiment, the second laser 81*b* is tunable, while the first laser 81*a* further includes an external wavelength selection element in an external cavity configuration. According to yet another embodiment, the first and second lasers 81*a*, 81*b* are both tunable. In a specific embodiment, the tunability may be achieved by current tuning at a fixed junction temperature for a diode laser, or by tuning the laser drive current at a fixed temperature.

The lasers 81*a*, 81*b* are controlled by laser control electronics 115 that are configured to provide the tuning capability as understood by a person of ordinary skill in the art. The lasers 81*a*, 81*b* may be mounted in butterfly packages, which are themselves mounted to a circuit board 105. Each butterfly package includes a number of pins arranged in a single-sided or double-sided configuration.

According to one embodiment, the first optical isolator 130*a* is in the first optical path between the first laser 81*a* and the multiplexer 83, and the second optical isolator 130*b* is in the second optical path between the second laser 81*b* and the multiplexer 83. The first laser 81*a* of the laser light source 100 may be optically coupled to the first optical isolator 130*a* and the second laser 81*b* of the laser light source 100 may be optically coupled to the second optical isolator 130*b*.

The optical isolators 130*a*, 130*b* are optical components that transmit light in only a certain direction while blocking light traveling in the opposite direction (unidirectional transmission). The unidirectional transmission capability of the optical isolators 130*a*, 130*b* inhibits unwanted feedback into the gain medium of the respective lasers 81*a*, 81*b*, which otherwise can destabilize the frequency and/or amplitude output of the laser. The optical isolators 130*a*, 130*b* may be either polarization dependent or polarization independent. According to one embodiment, the first optical isolator 130*a* is optimized for operation in a spectral region centered about λ1 and/or the second optical isolator 130*b* is optimized for operation in a spectral region centered about λ2. In another embodiment, the outputs of both optically isolated lasers are optimized to be similarly aligned in polarization state up to the point of injection into the non-linear optical (frequency conversion) crystal.

According to one embodiment, the first optical isolator 130*a* is optically coupled in as close as possible proximity with an emitting aperture of the first laser 81*a*. For example, an input 131*a* to the first optical isolator 130*a* may be closely coupled to an exterior face of an output coupler 111*a* of the first laser 81*a* to within a few millimeters. For example, at a distance, $d_1$, of about 0.01 mm to about 5 mm; at a distance of about 0.05 mm to about 2.5 mm; or at a distance of about 0.1 mm to about 2 mm. According to another embodiment, the second optical isolator 130*b* may also be optically coupled in as close as possible proximity with an emitting aperture of the second laser 81*b*. For example, an input 131*b* to the second optical isolator 130*b* may be closely coupled to an exterior face of an output coupler 111*b* from the second laser 81*b* to within a few millimeters. For example, at a distance, $d_2$, of about 0.01 mm to about 5 mm; at a distance of about 0.05 mm to about 2.5 mm; or at a distance of about 0.1 mm to about 2 mm. The output coupler 111*a* is configured to transmit a portion of the circulating intracavity optical power from the gain medium of the first laser 81*a* to generate a useful output in the form of the first laser beam at the wavelength λ1. The output coupler 111*b* is configured to transmit a portion of the circulating intracavity optical power from the gain medium of second laser 81*b* to generate a useful output in the form of the second laser beam at the wavelength λ2.

Optical isolation of at least 30 decibels (dB) should be achieved in each of the individual lasers 81*a*, 81*b* in as close as possible proximity to the gain medium of the lasers 81*a*, 81*b* prior to fiber coupling of the individual isolated outputs. The close proximity reduces the probability of laser mode-hopping and/or instability in output frequency for the lasers 81*a*, 81*b*. In particular, high optical isolation is required to prevent feedback into the laser from downstream sources, including fiber imaging optics, fiber ends, the non-linear optical crystal collimating optics, and the frequency conversion non-linear optical crystal faces and bulk media itself.

When present, an external wavelength selection element (not shown) may be optically coupled in close proximity to its respective optical isolator. Accordingly, the wavelength selection element in an external cavity configuration may be optically coupled at a distance within the range of about 0.1 mm to about 5 mm to its respective optical isolator. For example, the wavelength selection element may be optically coupled at a distance of about 0.2 to about 3 mm; or at a distance of about 0.25 mm to 2 mm. In one embodiment, second laser 81*b* further includes an external wavelength selection element in an external cavity configuration optically coupled to an external surface of the second optical isolator 130*b* at a distance within the range of about 0.1 mm to about 5 mm relative to the external surface of the second optical isolator 130*b*.

The multiplexer 83 may be optically coupled to the first and second optical isolators 130*a*, 130*b* by first and second polarization-maintaining optical fibers 120*a*, and 120*b*, respectively, to provide a multiplexer output polarized with respect to the favorable axis associated with the nonlinear optical crystal 84. Further, in another embodiment, the multiplexer 83 is optically coupled with the nonlinear optical crystal 84 using a third polarization-maintaining optical fiber 120*c*.

The previously described temperature stabilization of the thermal enclosure provided by the temperature control system operates to reduce the frequency drift of the lasers as well as maintain a constant power level in the converted wavelength ($\lambda 3$). The temperature stabilization also helps to reduce crosstalk in the various control electronics that control the individual laser temperatures and drive currents. Temperature stabilization also helps to maintain the frequency conversion crystal in a either heating or cooling mode, reducing the intervals in which the control circuit switched between the two modes.

In various typical embodiments according to the present teachings, the operating temperatures of the lasers 81*a*, 81*b* and of the non-linear crystal 84 are themselves controlled and stabilized, in a local sense, independently of the temperature control of the thermal enclosure. For instance, the temperature of each laser diode may be controlled independently of all other controlled temperatures in order to both tune and stabilize the wavelength of light emitted by that laser. As another example, the crystal temperature of the nonlinear crystal 84 may be controlled independently of the other controlled temperatures to enable efficient phase matching of the three wavelengths. As described subsequently, the nonlinear crystal may be mounted on a dedicated mount including a heat sink, a thermoelectric temperature controller and a temperature sensor. In similar fashion, each laser diode may be disposed on its own similar dedicated temperature-controlling mounting apparatus. Typically, however, commercially available diode lasers are available in integrated packages that include their own internal temperature control and temperature sensing elements. Dedicated electronic logic circuitry may be associated with each such temperature-controlled component so as to receive a signal indicating the temperature of the component and to provide a control signal (voltage or current) to the temperature controlling element of the component so as to minimize deviations of the sensed temperature from a respective set-point temperature. Each set of dedicated electronic logic circuitry may communicate with or may be controlled by the system computer. The temperature control of each of the lasers, crystal and possibly other components only locally effects the respective immediate environment of each respective component. These controlled component temperatures have little measurable effect on the independently controlled temperature of the thermal enclosure overall volume.

Figure 7:
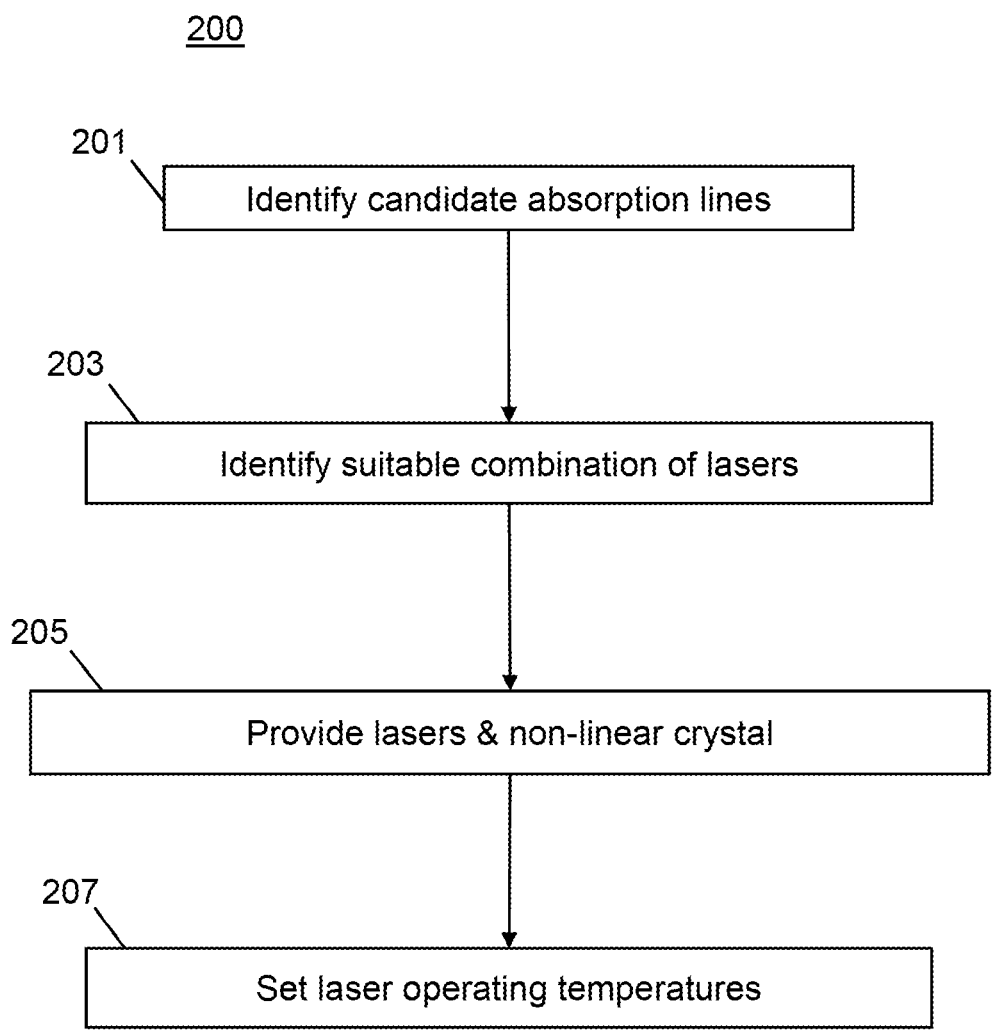
FIG. 7 is a flow chart of a method in accordance with the present teachings for designing a laser light source for use in mid-infrared absorption measurements of the concentration of a target gas.

FIG. 7 is a flow chart of a method 200 in accordance with the present teachings for designing a laser light source for use in mid-infrared absorption measurements of the concentration of a target gas. In Step 201, a set of candidate mid-IR absorption lines are first identified. Any such candidate lines should have a suitable value of specific absorbance. A "suitable" specific absorbance value is one that yields, when light is passed through an available path length within a gas cell containing an expected concentration of the target gas, a percentage light attenuation that is large enough so as to produce a measurable dip in detected light intensity but not so great as to reduce the amount of detected light close to nil. A reasonable rule of thumb is that the percentage of laser light absorbed should be in the range of about 20% to 80%. The available path lengths within the gas cell 74 are approximately the set of values given by 2 nL, where L is the inter-mirror distance and n is an integer between 1 and about 30 that represents the number of round-trip passes through the cell. Candidate mid-IR absorption lines should also be sufficiently removed in wavelength (or, equivalently, frequency or wavenumbers) from absorption features of other gases (notably water vapor) so that there is no significant overlap between the candidate target lines and the potentially interfering features.

Once candidate absorption lines have been identified in Step 201 of the method 200, the next step, step 203, is to identify suitable combination of (a) a wavelength-stabilized laser, (b) a scanning laser and (c) a non-linear crystal that are capable, in combination, of generating a DFG wavelength that may be swept over one or more of the candidate absorption lines. Generally, a sub-set of the candidate absorption lines will be eliminated at this point, since suitable combinations of hardware (two lasers and a crystal) may not be available. If the two lasers are chosen from diode lasers, then several different nominal emission wavelengths may be available for each type of diode laser. Further, the emission wavelength of most diode lasers may be adjusted or tuned within a certain range during normal operation. Tuning may be accomplished either by adjusting the laser temperature or drive current. The goal of Step 203 is to choose a combination of lasers and a non-linear crystal such that it is possible to sweep the wavelength of one of the lasers—the scanning laser—whose emissions are input to the crystal such that a difference-frequency-generated mid-IR wavelength generated by the crystal fully sweeps or traverses across a candidate absorption line. The sweep should also be sufficiently wide so as to include sufficiently wide bounding wavelength portions (on either side of and contiguous with the absorption line portion) sufficiently removed from the absorption line center such that a reliable "baseline" may be calculated (see further discussion below). For instance, if $w_h$ is the half-width (i.e., full width at half maximum) of the absorption line feature, each bounding or baseline wavelength portion should include a region removed from the line center by at least $2w_h$.

Once the lasers and crystal have been identified, a gas sensor system using the identified wavelength-stabilized laser, scanning laser and non-linear crystal is provided, in Step 205, so as to generate the mid-IR wavelength. In Step 207, the laser operating temperatures and drive currents are set so that the difference-frequency-generated emission wavelength is removed from the maximum absorbance wavelength of an absorption line by a certain pre-determined wavelength increment. This pre-determined wavelength difference, relative to the absorbance maximum of a targeted absorption line, serves as a starting position for subsequent wavelength sweeps across the absorption line (and possibly across other absorption lines) and includes a bounding or baseline portion as described above. The choice of the pre-determined wavelength difference ensures that the DFG wavelength may be swept over the one or more absorption lines by only current-driven sweep of scanning laser.

Using methods similar to that described above, the inventors have identified wavelength ranges of approximately 3200-3400 nm for detection of $CH_4$ and 4200-4700 nm for detection of CO, $N_2O$ and $CO_2$. In order to generate mid-IR light useful for detecting CH$_4$, first and second lasers emitting in the 1000-1100 nm range and in the 1500-1600 nm range, respectively, may be employed. In order to generate mid-IR light useful for detecting CO or N$_2$O, first and second lasers emitting in the 1100-1100 nm range and in the 1500-1600 nm range, respectively, may be employed. In particular, the CO spectrum includes approximately 5-10 rotationally resolved absorption lines in the range from approximately 4570 nm to 4650 nm that are useful, either individually or in combination, for detection of this species. As another example, the N$_2$O spectrum comprises approximately 10 absorption lines in the range from approximately 4510 nm to 4555 nm that are useful, either individually or in combination, for detection of this species.

FIGS. 8A-8B are, respectively, schematic plan and elevation views of a crystal, filter and lens assembly 252 in accordance with various embodiments of the present teachings. The assembly 252 may be employed to maintain the non-linear crystal 84, laser filter 85 and a focusing lens 87a in precise position with regard to one another and with regard to the optical fiber 95 within an optical chamber module 72. As illustrated, the assembly 252 includes a mounting plate or platform 260 that supports a non-linear crystal 84, a laser-line rejection filter 85 and a collimating lens 87b. The non-linear crystal 84 held in place within a crystal holder device 262 that also serves as a thermal heat sink for homogenizing the temperature of the crystal and minimizing temperature fluctuations of the crystal. The crystal holder device 262 is held in close thermal contact with a thermo-electric temperature control device 264 which is able to maintain the crystal holder 262 and non-linear crystal at a predetermined temperature. The crystal holder 262 may comprise a top member 266 and a bottom member 267 which, together, clamp the crystal 84 in place between them. The crystal holder, crystal, thermo-electric temperature control device and mounting plate or platform may be held in tight thermal contact by fasteners, such as screws. Preferably, the crystal holder device 262, including both the top member 266 and bottom member 267, is fabricated of a material with high thermal conductivity, such as, for instance, copper.

The laser line rejection filter 85 (FIGS. 8A-8B) is disposed at an angle relative to the path of the beam emerging from the crystal 84 in order to reflect light of the wavelengths λ1 and λ2 away from the optical path while transmitting difference-frequency-generated light of wavelength λ3. The two faces of the filter are preferably non-parallel to one another (that is, the filter is slightly wedge-shaped or wedged in cross section) in order to eliminate or minimize etalon interference effects. After passing through the filter 85, the light λ3 light is collimated by lens 87b in preparation for traversing through the gas cell 74.

The crystal, filter and lens assembly 252 also provides support and alignment for an optical fiber or fiber optic cable 95 that delivers the multiplexed laser light generated in the laser chamber module. A bracket 269 on the mounting plate or platform 260 serves to hold the fiber 95 and focusing lens 87a in proper optical position with respect to the non-linear crystal so that the laser light may propagate completely along the entire length of the non-linear crystal 84. The mounting plate or platform 260 provides correct positioning and alignment for the various optical components shown in FIGS. 8A-8B, with respect to one another.

Figure 9:
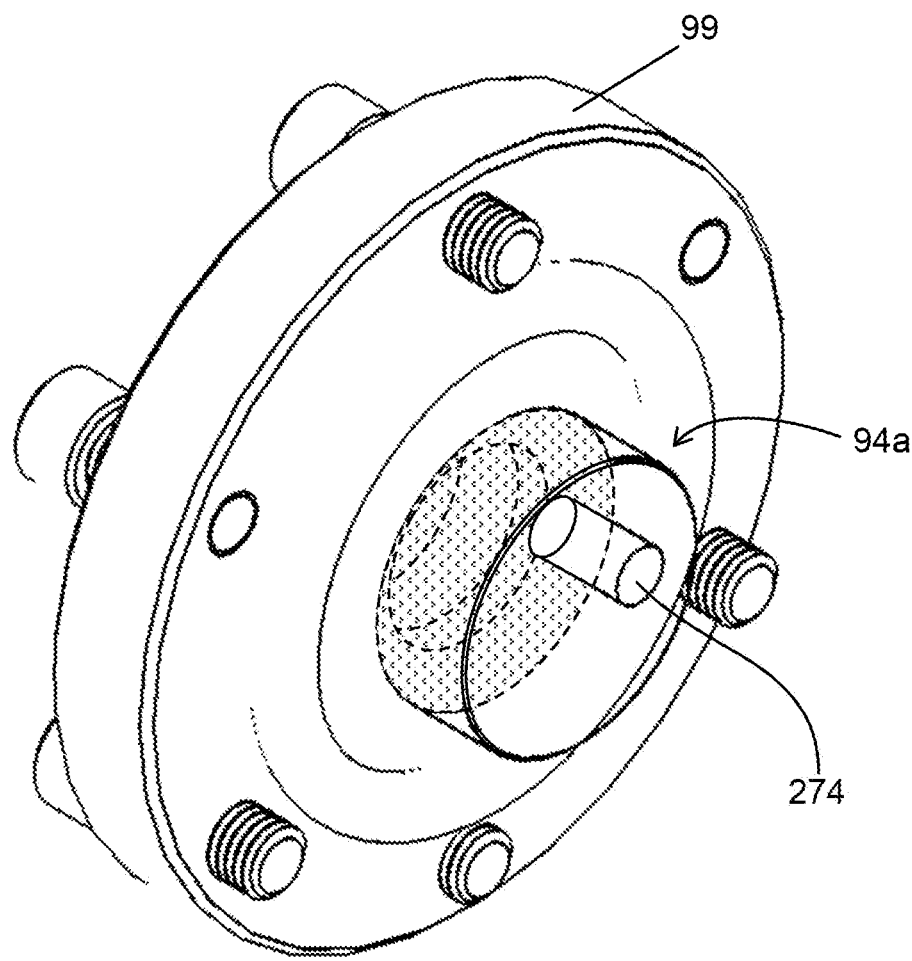
FIG. 9 is a perspective view of a front entrance port of a gas cell for a gas sensor in accordance with the present teachings.

FIG. 9 is a perspective view of a portion of the front end assembly 246 of the gas cell 74 showing the front mirror 94a disposed in a mounting flange 99. The mid-IR light from the optical chamber module 72 and the attenuated mid-IR light directed back to the optical chamber module both pass through a small portion 274 of the front mirror 94a. For instance, the mirror 94a may comprise a mid-IR transparent substrate having a mirror coating on one face. A small portion of that face may lack the mirror coating thereby permitting light to both enter and exit the gas cell through the un-coated portion and through a portion of the substrate. Alternatively, the light may pass through a hole that passes completely through the mirror 94a. Such a hole would also permit the flowing sample gas to exhaust from the gas cell through the front mirror.

FIGS. 10A-10B are schematic illustrations of two alternative apparatus configurations and methods for sample gas flow within a gas sensor in accordance with the present teachings. Each of FIGS. 10A-10B illustrates, in schematic fashion, a gas cell 74 and an optical chamber module 72. Although the arrangement of optical components shown in FIGS. 10A-10B is similar to that illustrated in FIG. 5B, the arrangement of optics need not be as shown in these figures but, alternatively, could comprise an optical arrangements as shown in any of FIGS. 5A-5C or could comprise any combination, hybrids or other modification of such optical arrangements.

In the system configuration illustrated in FIG. 10A, a window 89 is disposed between the interior of the optical chamber module 72 and the interior of the gas cell 74, thereby preventing gas communication between the optical chamber module and the gas cell. The window 89 could be affixed to a wall of a housing of the gas chamber module or to a wall of a housing of the optical chamber module. During assembly of the system, the optical chamber may be flushed with an inert gas (e.g., nitrogen) and then sealed. Thus, in the configuration shown in FIG. 10A, the gas cell 74 and optical chamber module 72 are fluidically isolated from one another. Accordingly, sample gas exhausts through a gas outlet port 242a of a front end assembly 246 of the gas cell to exhaust tubing (not shown) prior to reaching the optical chamber module. The exhaust tubing may be connected, at its opposite end, to a vacuum pump whose operation maintains the sample gas at a controlled reduced pressure. Using such a configuration, the interior of the optical chamber module may be maintained as a sealed environment for the prevention of contamination or degradation of the precision optical components by dust or other particulates or corrosive gases.

The first gas flow configuration, as illustrated in FIG. 10A, is suitable for many purposes. The inventors have discovered, however, that the accuracy of measurements of certain analyte gases—for instance, methane (CH$_4$), carbon monoxide (CO), carbon dioxide (CO$_2$)—can be compromised by outgassing of the same respective chemical species by materials within the optical system. Some common materials which may be used in the optical chamber and which may contribute to outgassing include: machined bare aluminum, machined and anodized aluminum, copper, stainless steel screws and washers, epoxies, circuit board, wires and cables, lubricants and greases. The inventors have found that, over time, using a sealed optical chamber, the concentration of these gases builds up. Gradually, the build-up of these background interferent gases can contribute an undesired and significant background signal to the absorption signal coming from the sample gas flowing through the gas cell. Whereas the sample gas in the gas cell 74 is generally maintained at a controlled sub-ambient pressure, the contaminating gas of the same species in the optical chamber module 72 will generally be at ambient (e.g., atmospheric) pressure. Because the line width of mid-IR absorption lines is highly sensitive to pressure in these pressure ranges, the presence of the ambient pressure species will contribute a broad background absorption feature that overlaps the position of the target absorption line and that increases with time.

The system configuration of FIG. 10B is provided in order to address the potential problem of interference from outgassing species. In gas flow configuration shown in FIG. 10B, the interior volumes of the gas cell 74 and the optical chamber module 72 are not isolated from one another. Instead, the two volumes are fluidically connected, and the sample gas flows through the gas cell and into the optical chamber. The sample gas then exits the optical chamber through a gas outlet port 242b provided through a wall of the optical chamber module and that is connected, at its opposite end, to the vacuum pump. Therefore, using the system configuration shown in FIG. 10B, the optical chamber module interior is maintained at the same pressure as the interior of the gas cell, and the gas residing in the optical pathway of the optical chamber module is continuously flushed out by the sample gas. Thus, any background interferent gases given off by the materials in the optical chamber do not build up. Rather, these background gases are flushed out of the optical chamber by the flowing sample gas. Accordingly, there is no resulting build-up of a background absorption signal from these interferent gases.

Modes of Operation

Other conventional laser-based systems which strive for high sensitivity measurements of infrared transmittance employ Frequency Modulation Spectroscopy (FMS). In the FMS technique, the emission frequency of the laser is modulated across the absorption feature and the resulting signal is expanded in a Fourier series. The coefficients of the expansion are denoted as harmonics. The even harmonics each exhibit a maximum and the odd harmonics each exhibit a zero-crossing at the center of an absorption line. In addition to a sample gas cell, a reference gas cell is also employed. The reference gas cell contains a sample of the target gas of interest. Line-locking of the laser line to the line center of the absorption feature of interest is accomplished by monitoring the third harmonic of the signal of light transmitted through the gas in the reference cell. This technique therefore requires splitting the laser beam before the sampling cavity.

Although the FMS technique can improve sensitivity, it does pose some practical difficulties. As mentioned, a reference cell is required. Additionally, a "zero" gas, which comprises a purified gas essentially free of the target analyte gas, may need to be occasionally flushed through the sample cell in order to determine a baseline response of the system in the absence of the absorption feature of interest. The sensitivity is often limited by interference patterns attributable to the optics of the system. Various methods of eliminating interference patterns include mechanical approaches, specialized modulation waveforms, specialized modulation frequencies, multiple modulation frequencies. The sensitivity may also be limited by fluctuations in laser intensity, and more importantly by fluctuations in background levels of the second harmonic signal. A second detector and additional beam path may be required in order to account for these fluctuations.

In order to overcome the additional cost, complexity, space and materials requirements associated with providing reference gas, zero gas, an additional cell, additional optics and an additional detector, the inventors have developed a method and system that employs direct mid-IR absorption measurements. The method includes repeatedly sweeping the wavelength of difference-frequency generated light across an absorption feature of a target gas. FIG. 11A is a graph of a single cycle of an exemplary cyclical laser current-sweep waveform as applied to a laser of a light source of a gas sensor system in accordance with the present teachings. FIG. 11B is a graph of an example of a detector signal as may be generated upon application of the current-sweep waveform of FIG. 10A to a laser of a light source of the system. Typically, this cyclical drive current will be applied to only one laser, since the difference-frequency-generated mid-IR wavelength may be made to vary by changes to either laser. The cyclical waveform 300 representing the laser drive current versus time comprises a first portion 301a in which no current is applied to the laser and, accordingly, the laser does not emit light. The cyclical waveform 300 also comprises a second ramp portion 301b in which the laser drive current is linearly increased, by control electronics, from an initial lower value to a greater ending value. Alternatively, the laser drive current may be decreased during the ramp portion from an initial relatively greater value to lower ending value. As still another alternative, the drive current may be first ramped upward and then subsequently ramped downward so as to form a "sawtooth" pattern. Other variations are possible. The waveform may be repeatedly applied at a certain rate, for example, 200-300 Hz.

The emission wavelength (either $\lambda 1$ or $\lambda 2$) of both the laser whose drive current is modulated and the difference-frequency-generated wavelength ($\lambda 3$) vary in concert with the drive current. Accordingly, the horizontal axis of FIG. 11B represents not only time during application of the cycle but also represents wavelength (or, alternatively, frequency) during the time that the drive current is ramped. The wavelength increases in the direction of increasing laser current (and time). Therefore, the graph proceeds from higher optical frequency (at time=0) to lower frequency. The graph 302 of the detector signal (voltage or current, depending on the type or mode of operation of the detector) measured during this cycle thus represents a record of the emission intensity of $\lambda 3$ as modified by any sample gas absorption or other losses and by superposition of random "noise". The detector signal is digitized at a plurality of discrete time points—for example, 1024 points—within each repetition of the waveform 300.

There will be no laser emission during the portion of the drive-current cycle 301a that no drive current is applied. Assuming that the detector is a photo-conductive type, the detector signal reverts to a non-zero background voltage, $V_{offset}$ during these times. The background voltage may be determined from sections 303a of the detector signal 302. During the portion of the cycle 301b during which the drive current is ramped, both the emission wavelength and the output power of the light source are caused to vary, thus yielding the generally sloping section 303b of the graph of detector signal. In the absence of any gaseous mid-IR absorption features, the graph of the detector signal obtained during the ramped portion 301b of the drive current cycle will follow the trend of the generally sloping "baseline" 308 (which, for clarity of presentation, is shown with extrapolated extensions at both ends in FIG. 11B). The trend of the baseline follows the variation of laser emission power with varying wavelength (as the drive current is ramped) as modified by any system losses, but not by gaseous absorption. System losses may be related to a variety of factors such as transmission efficiencies of any lenses and filters, scattering or stray light losses and etalon effects, some of which may be wavelength dependent.

All or a portion of the curvature in baseline 308 may result from etalon effects. To reduce etalon effects, various optical elements in the beam pathways may be wedge-shaped (for instance, the laser line rejection filter 85 shown in FIG. 5, FIG. 6 and FIG. 8) or may be tilted or otherwise angled at an angle to the beam propagation (for instance, fiber end facets, various lenses, etc.). Although such etalon effects may be reduced, it is not generally possible to entirely eliminate them. Nonetheless, any remaining etalon effects may be removed by fitting of a polynomial function to the curved baseline, provided that these etalon effects are stable—that is, do not vary with time. Temperature stabilization, as previously described, can stabilize the residual etalon effects, thereby ensuring the stability of the polynomial baseline fit and, consequently, of the subsequent peak fits. For this reason, the insulated thermal enclosure system 40 (FIGS. 2-3) and heat exchanger system (FIG. 4) are provided so as to thermally isolate all optical components and stabilize their temperature to within 0.1 K.

The graph 302 represents a hypothetical signal from a single wavelength scan as might be obtained in a single sweep of the laser drive current from low to high (or high to low). The detector signal corresponding to any single scan may include a significant degree of random "noise", such as electronic or thermal noise generated in the detector. In practice, the signals obtained in several successive scans are co-added in order to average the random fluctuations in the noise and thereby improve the signal-to-noise characteristics. Presently available diode lasers are capable of being current modulated at very high repetition rates. As one example useful in the present teachings, the drive-current pattern shown in FIG. 11A may be repeated at a rate of 200-300 Hz, thus yielding 200-300 samples of the graph 302 per second. When these are co-added, a resulting clean signal such as that shown in FIG. 12A may result.

Graph 302 (FIG. 11B) includes two hypothetical features 304 and 306 in the detector signal that correspond to respective infrared absorption lines of one or more gases. Such absorption lines appear as dips below the baseline 308 in the plot of detector signal versus wavelength. If the constant value of the null signal, $V_{offset}$, is subtracted pointwise from the vertical coordinate of each point on the graph section 303b, then there results a set of points whose vertical coordinates, $\Delta V$, represent the response of the detector to detected light, plus a noise contribution that may be reduced by co-adding. The baseline 308 may be modeled as a polynomial fit to the points away from the absorption features 304, 306. Likewise, the value of the null signal, $V_{offset}$, may be determined by averaging of values in regions 303a. Let the difference between the baseline vertical coordinate value and $V_{offset}$ at the wavelength of an absorption feature be denoted by $\Delta V_0$ and let the difference between the actual signal value (the attenuated signal) and $V_{offset}$ at the same wavelength be denoted by $\Delta V_p$ (see FIG. 11B).

The quantity $\Delta V_0$, as defined above, is representative of the detector response to light that would be observed in the absence of the absorption feature and thus obviates the need to run a "blank" or "zero gas" reference sample. The quantity $\Delta V_0$ is representative of the detector response to the actual attenuated light. Accordingly, it is possible to construct a relationship—by means of an instrumental calibration—between the ratio ($\Delta V_p/\Delta V_0$) and the transmittance, t, where t is as defined in the Beer-Lambert law:

$$t = \frac{I_p}{I_0} = e^{-\sigma l N} \qquad \text{Eq. 3}$$

in which $I_0$ is the intensity or power of light as input to the sample gas, $I_p$ is the intensity or power of the light upon transmission through the gas, $\sigma$ is the absorption cross section per particle, l is path length through the sample and N is the number of absorbing particles per unit volume. In general, it will be true that $$\frac{I_p}{I_0} = a_0 + a_1 \frac{\Delta V_p}{\Delta V_0} \qquad \text{Eq. 4}$$

where the constants $a_0$ and $a_1$ may be determined by instrumental calibration using, for instance, a calibration gas of known concentration. Since the path length, l, is set by experimental design and the quantity $\sigma$ is available from reference data, the quantity N at the pressure of the experiment may be calculated. This latter quantity may be corrected to ambient pressure, if desired, using the ideal gas law. Even if the value of $\sigma$ is not accurately known, temporal variations in the concentration of a target gas may, nonetheless, be precisely monitored.

Figure 12A:
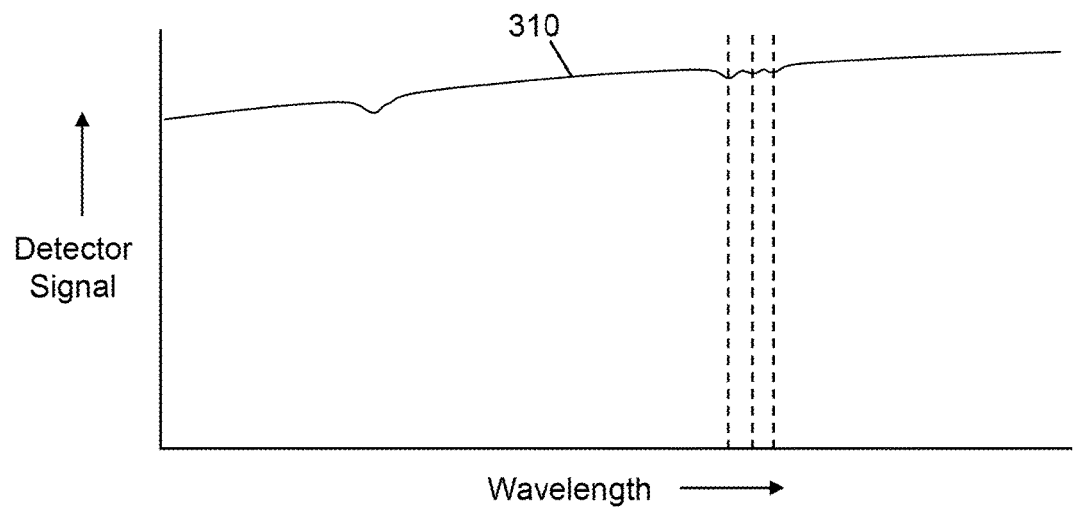
FIG. 12A is a graph of a detector signal obtained from detection of methane using a gas sensor system in accordance with the present teachings.
Figure 12B:
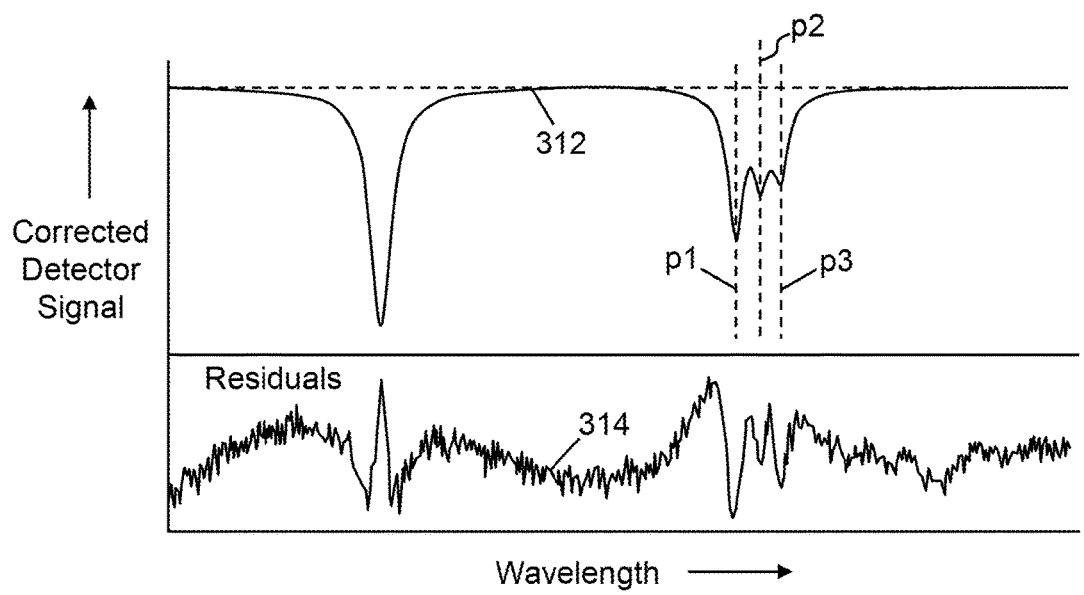
FIG. 12B is graph of a corrected signal of methane obtained by fitting a baseline to and removing the fitted baseline from the detector signal data illustrated in FIG. 11A and further illustrating quality of fit of synthetic peaks to the features of the corrected signal.

The calculations described above are generally performed on co-added data so as to improve the signal-to-noise ratio. FIG. 12A is a graph 310 of a detector signal obtained from detection of methane using a gas sensor system in accordance with the present teachings. The upper portion of FIG. 12B is graph 312 of a corrected signal of methane obtained by subtracting the null signal, fitting a polynomial baseline to the data and removing the fitted baseline from the raw detector signal data. The triplet absorption feature, represented by separate partially-resolved absorption features at positions denoted by p1, p2 and p3, is from methane absorption; the single absorption line on the left is from water. After baseline removal, all of the absorption features shown in the top portion of FIG. 12B may be modeled by a set of Lorentzian or Voigt model profiles. The residuals to an actual fit are shown, at greatly expanded vertical scale, as curve 314 in the lower portion of FIG. 12B. The fitted profiles may then be used to calculate the quantities ($\Delta V_p/\Delta V_0$) and ($\Delta I_p/\Delta I_0$) discussed above. The methane and water concentrations may then be automatically calculated, using Eq. 3, by the internal system computer and software and displayed to a user.

The above discussions relating to data reduction implicitly assume that absorption features are sufficiently well-resolved (with regard to absorption features of the same and other species) to be measureable, that these features can be unambiguously assigned to specific gas species, that these features may be sufficiently scanned across their breadth so as to enable adequate baseline fitting and spectral profile fitting and that the absorption features are reproducible in terms of their position and shape. Infrared absorption lines may obtain their theoretical minimum line width of approximately 15 MHz only at absolute zero pressure and absolute zero temperature. The line widths of real IR spectra of gases at finite temperatures and finite ambient and sub-ambient pressures broaden in proportion to the square root of absolute temperature and in direct proportion to pressure, P. The natural line widths (i.e., the Doppler broadened line widths in the absence of significant pressure broadening) of rotationally resolved lines at 298 K may range from several tens of MHz to several hundred MHz, depending on the molecular weight of the species of interest. Superimposed on this natural line width, the pressure broadening may be on the order of one to several megahertz per Torr. Shifts in line center positions may also occur with changes in pressure and temperature, but the effects of such shifts are much smaller than the effects of broadening.

Figure 13:
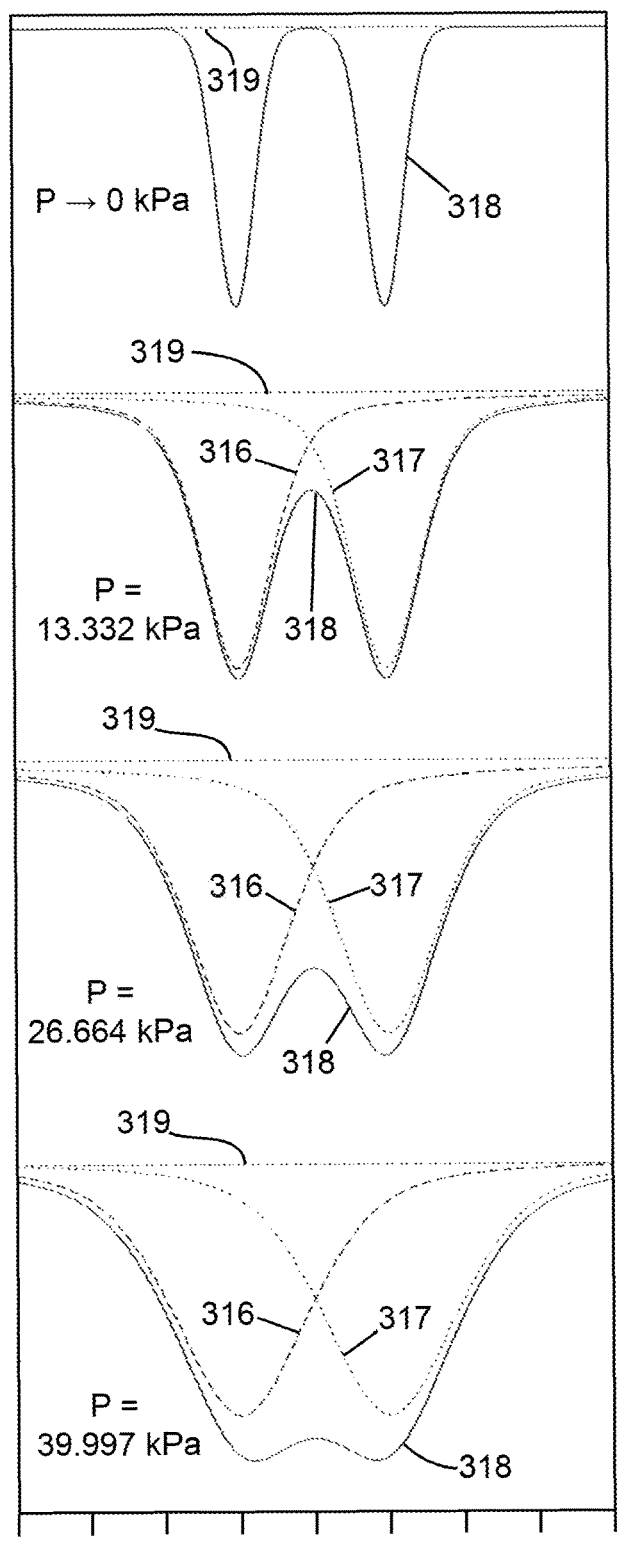
FIG. 13 is a set of Lorentzian curves illustrating hypothetical spectral changes due to pressure broadening.

Because of the temperature and pressure dependencies of line widths noted above, tight control of sample gas temperature and pressure may be required to prevent unacceptably high uncertainties in the calculation of model peak fits used for calculating the strength of light absorption. The sensitivity of absorption profiles to pressure is illustrated by the calculated results shown in FIG. 13, in which a transmittance spectral envelope resulting from two absorption neighboring lines is shown at various pressures. The calculations whose results are illustrated in FIG. 13 assume the existence of two hypothetical lines having natural (i.e., Doppler-broadened) line widths of 300 MHz that are spaced 1000 MHz apart and whose line widths (full width at half-maximum, or FWHM) both increase at a rate of 2.6 MHz/Torr. These Doppler-broadened line widths, $\Delta\omega$, are consistent with absorption lines of methane (mass, m, of 16 Da) near 3.17 nm (frequency, $\omega$, of about 94.6 THz) as calculated at temperature, T, of 313° K from the equation $$\frac{\Delta\omega}{\omega} = \frac{1}{c}\left(2\ln 2 \frac{kT}{m}\right)^{1/2}. \qquad \text{Eq. 5}$$

The line width broadening rate of 2.6 MHz/Torr is consistent with an average of the experimentally measured pressure-broadening coefficients of several methane mid-IR lines as provided by Predoi-Cross et al (Journal of Molecular Spectroscopy, 236, pp. 201-215, 2006). Thus, the hypothetical spectra illustrated in FIG. 13 provide an example of how the envelope of closely-spaced methane mid-IR lines would be expected to change as the pressure of a sample gas (comprising essentially air plus methane) changes. The uppermost curve shown in FIG. 13 is calculated using component Gaussian lines as would be expected to occur in the limit of zero pressure. The other curves are calculated using pseudo-Voigt profiles (the average of a Gaussian curve and a Lorentzian curve having identical FWHM values).

The curves 316 and 317 in the lower three panels of FIG. 13 represent the pressure broadened component line profiles; the curves 318 represent the spectral band or envelope calculated as the sum of the two component profiles. The baselines (100% transmission) of the various spectral envelopes are shown as horizontal lines 319. The component line profiles in the top panel (limiting pressure of zero) are indistinguishable from the envelope and, thus, are not shown. The spectral absorption envelopes illustrate in FIG. 13 show that line resolution is rapidly lost as pressure increases from 0 Torr to 300 Torr. At a pressure of 400 Torr (not shown), the envelope is essentially flat (at the illustrated scale) between the positions of the two lines. Note also that there may be a small shift of the line center positions with pressure. In the case of methane, this shift is approximately one order of magnitude less than the pressure broadening and is therefore neglected in the depictions of FIG. 13.

In the present example (FIG. 13), the pressure broadening is such that the FWHM line-width becomes approximately equal to the line separation at a pressure of 300 Torr. Thus, at this pressure, a peak-fit calculation of, for instance, the amplitude or peak area of curve 316 may not have the desired 0.1% precision in the presence of the interfering peak 317. The rate of line broadening with increasing pressure may be even more rapid than suggested by the curves in FIG. 13, because the degree of Lorentzian character of the line shapes may increase with pressure. The increase in Lorentzian character may cause the wings of the peaks to broaden beyond the edges of the experimentally-probed spectral range, thereby also increasing the uncertainty in baseline fitting. Accordingly, the sample gas pressure should be maintained at or below a pressure at which the expected peak FWHM is equal to the average line width—in the illustrated case, below approximately 300 Torr.

The loss of resolution at increasing pressures suggests the desirability of maintaining a low sample gas pressure. However, additional considerations arise that provide a lower limit for optimal pressure. A first consideration is that, in order to maintain maximum instrument portability and minimum weight, the vacuum pump should not be too large. Thus, a compromise must be achieved between vacuum pumping capacity and system size and weight. A second consideration arises from the fact that, in practice, the number of absorbing molecules in the gas cell will decrease with decreasing pressure, thus causing the absorption envelope 318 to merge with the baseline 319 at zero pressure, and thus extinguishing the useable signal. (Note that the vertical scales of the spectral envelopes are normalized in FIG. 13 so as to appear to be the same height.) Thus, the sample gas pressure must be maintained above some minimum pressure—for instance, at a pressure above 100 Torr. Because of the indicated sensitivity of the line amplitudes, line shapes and line widths to pressure in this regime, the pressure should be maintained at a constant pressure—preferably to within 1 Torr.

Figure 14:
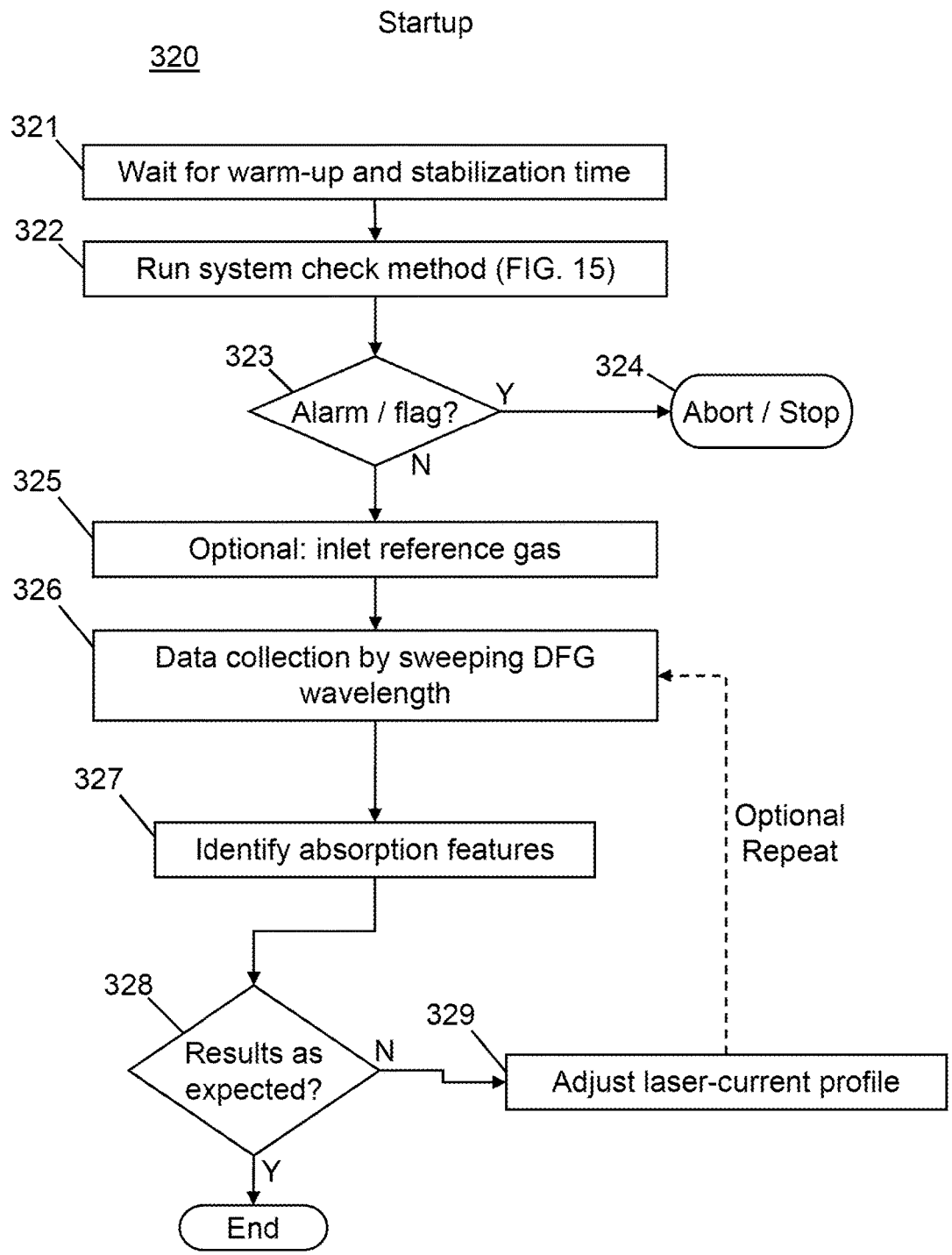
FIG. 14 is a flow chart of a method in accordance with the present teachings for commencing operation of a gas sensor that measures mid-infrared gas absorption.

FIG. 14 is a flow chart of a method in accordance with the present teachings for commencing operation of a gas sensor that measures mid-infrared gas absorption. In a first step, Step 321, sufficient time is allotted to allow the temperatures of the lasers, detector, non-linear crystal, gas cell and insulated enclosure to stabilize and, possibly, to allow the gas cell to be adequately flushed and to allow its pressure to stabilize. In the next step, Step 322, a system check operation (for example, see FIG. 15) may be performed. If it is determined, in Step 323, that the system check resulted in an error, then the startup procedure may need to abort (Step 324). If there are no errors, then, in an optional step, Step 325, a calibration or reference gas may be inlet to the system, for detection in the subsequent step, by opening a valve on a particular dedicated gas inlet port. This step may be bypassed if a target gas is available in the ambient environment to be readily detected and identified by the gas sensor. In the next step, Step 326, an initial or preliminary data collection step is performed by sweeping the DFG emission wavelength using a default waveform for controlling a laser drive current. This initial data collection step is a reconnaissance step to ensure that the expected absorption features are present and positioned correctly within the spectral window defined by the drive-current sweep. In Step 327 absorption features in the collected data are identified. This step may include various data reduction or manipulation processes such as spectral co-adding, baseline correction or curve fitting. It may also include automatic detection of the presence of absorption features and their locations. In the subsequent decision step, Step 328, the determined positions of identified peaks are compared to predetermined expected positions. If the absorption features do not occur at the expected positions to within a certain tolerance, then the method 320 branches to Step 329, in which the laser-current profile is adjusted in a fashion so as to bring identified absorption features to desired positions within the spectral profile. Optionally, the method may return back to Step 326 to verify that the adjustment was successful. If, in Step 327, the observed peaks do indeed occur at the expected positions to within the tolerance, then the method 320 ends.

Figure 15:
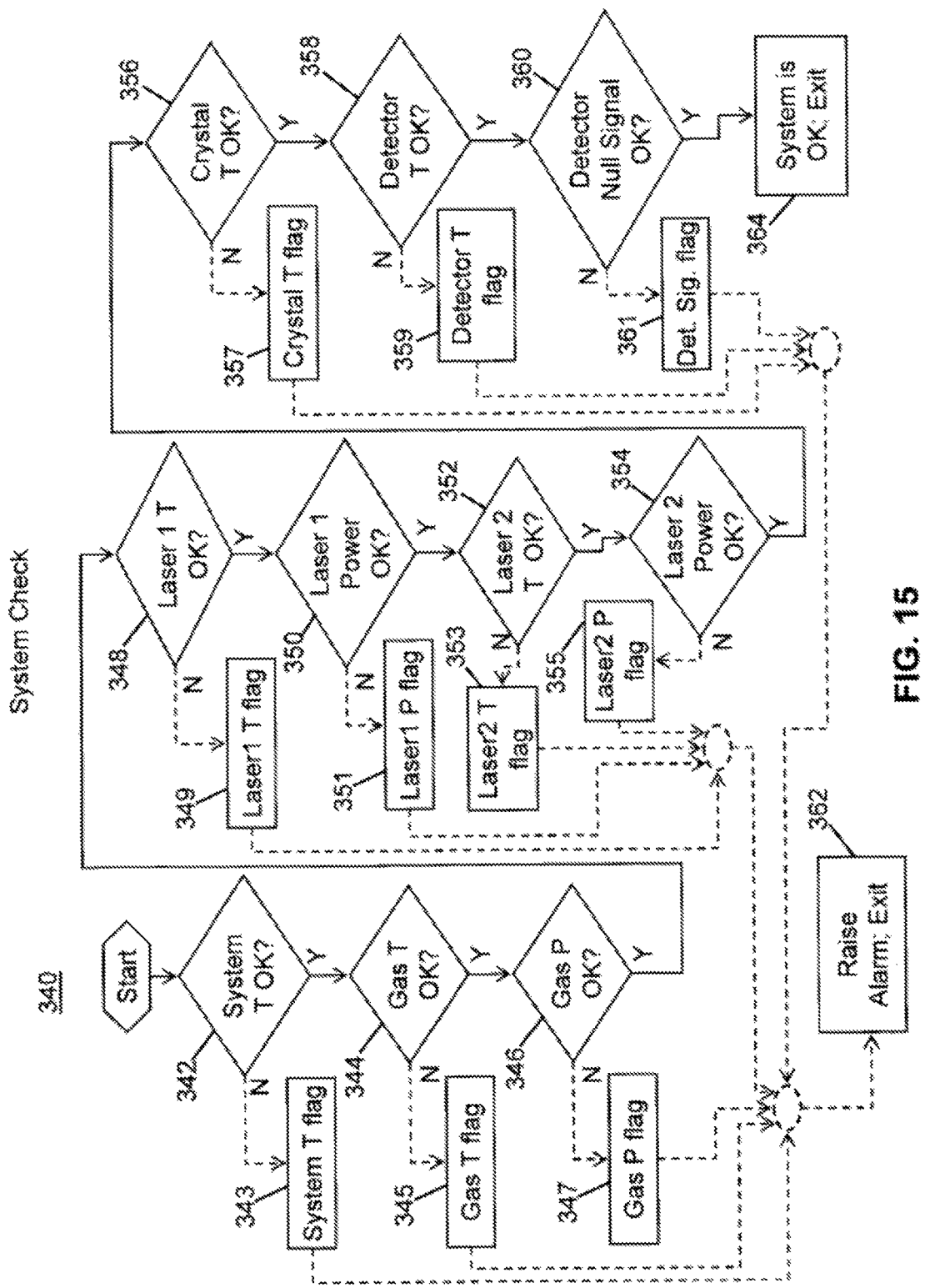
FIG. 15 is a flow chart of a method in accordance with the present teachings for performing a system check of a gas sensor in accordance with the present teachings.

FIG. 15 is a flow chart of a method in accordance with the present teachings for monitoring a gas sensor system that measures mid-infrared gas absorption. The method 340 schematically illustrated in FIG. 15 includes several measurement, comparison and decision steps, namely steps 342, 344, 346, 348, 350, 352, 354, 356, 358 and 360. In these steps, the readings of various sensors within the system are interrogated and each respective reading is compared to a nominal or expected value, with the results of the comparison used as input to a decision regarding which step is next executed. For instance, the system temperature (System T), sample gas temperature (Gas T) and sample gas pressure (Gas P) are measured and compared to respective nominal or expected values at step 342, step 344 and step 346, respectively. The system temperature may be measured by one or more thermocouples or thermistors within an insulated optical chamber module. The sample gas pressure may be measured by a pressure transducer which is in fluid communication with the interior of a gas cell. Further, the temperature of a first laser diode chip (Laser 1 T) and the power or intensity of light emitted from the laser diode chip (Laser 1 Power) may be measured and compared to respective nominal or expected values at step 348 and step 350, respectively. The temperature and power may be sensed by an onboard temperature sensor and photodetector included as part of an integrated package containing the laser diode chip. Likewise, the temperature of a second laser diode chip (Laser 2 T) and the power or intensity of light emitted from the second laser diode chip (Laser 2 Power) may be measured and compared to respective nominal or expected values at step 352 and step 354, respectively.

In step 356, step 358 and step 360 of the method 340, the temperature of a non-linear crystal for providing light by difference frequency generation (Crystal T), the temperature of a photo-detector (Detector T) and a detector null signal may be measured and compared to respective nominal or expected values. The crystal temperature may be provided, for instance, by a temperature sensor included in a thermoelectric cooler or thermo-electric temperature controller module with which the crystal is in thermal contact. The detector temperature may be provided by a temperature sensor included as part of a cooling portion of an integrated detector package.

After each of the previously discussed steps of method 340, a computer readable memory "flag" may be raised or set if, in the previously executed measurement, comparison and decision step, the relevant measured value was determined to be not in accordance with a nominal or expected value or range of values. For instance, if, in the measurement, comparison and decision step, Step 342, the system temperature is found to be not in accordance with a nominal temperature value or range of temperatures, then execution branches to Step 343 in which a "System T" flag is raised or set. Otherwise, execution continues on to the next measurement, comparison and decision step, Step 344. Likewise, specific flags may be raised or set in one or more of Step 345, Step 347, Step 349, Step 351, Step 353, Step 355, Step 357, Step 359, and Step 361. Each such flag may comprise a computer readable signal or memory value—such as a signal line voltage or a memory bit value—that conveys information about a specific respective sensor measurement. After a flag is set, execution may branch to Step 362 in which an alarm may be raised and the method concludes.

It should be noted that the steps listed in the method 340 in FIG. 15 need not be performed in the sequence shown and, in fact, need not be performed sequentially at all. For example, one or more groups of the steps 342, 344, 346, 348, 350, 352, 354, 356, 358 and 360 may be performed in parallel—perhaps simultaneously—by a plurality of dedicated circuits, processors, firmware module or software modules. Each such step may include feedback and control mechanisms—perhaps performed by a dedicated circuit, processor, firmware module or software module, as part of a normal control system. In such a case, the associated "flag" step (i.e., one of the steps 343, 345, 347, 349, 351, 353, 355, 357, 359 and 361) may be executed only when nominal control (for instance, successful control within certain nominal limits of temperature, pressure, or signal level) has failed.

Figure 16:
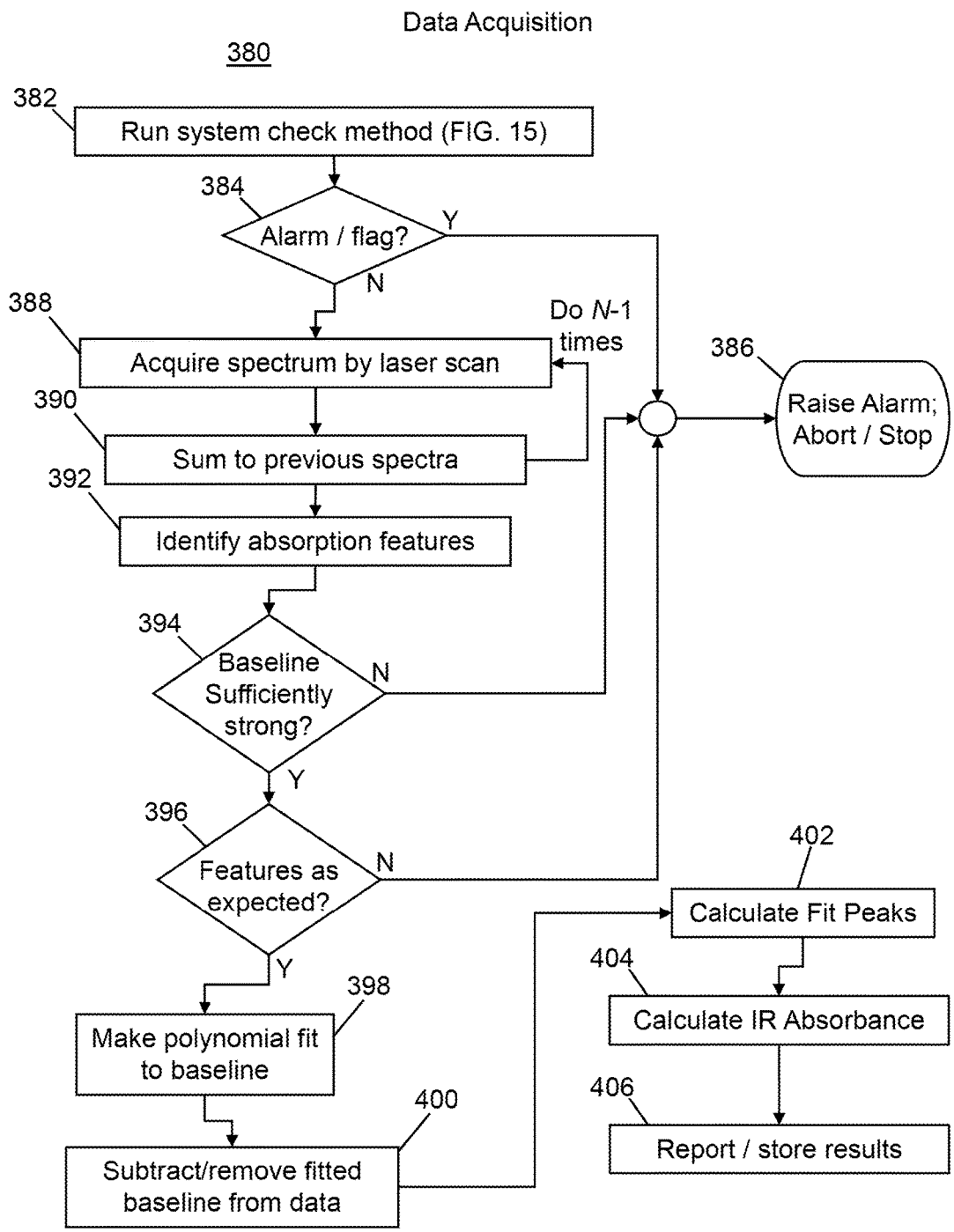
FIG. 16 is a flow chart of a method in accordance with the present teachings for acquiring gas concentration data using a gas sensor that measures mid-infrared gas absorption.

FIG. 16 is a flow chart of a method 380 in accordance with the present teachings for acquiring gas concentration data using a gas sensor that measures mid-infrared gas absorption. In the first step, Step 382, a system check (such as method 340 shown in FIG. 15) may be executed to determine if the system is ready to or capable of acquiring data. The results of the system check are assessed in Step 384, which branches execution to Step 386 if any alarms or flags were raised (thus indicating possible errors or problems). Step 386 may perform one more of the actions of raise a further alarm, provide notification of an error to an entity (such as a person) or aborting a measurement. If there are no errors or problems, Step 388 is executed, in which a directly measured absorption spectrum is acquired by, for example, the methods previously described in this document. In Step 390, the most recently acquired spectrum is summed to the running sum of previous spectra—that is, spectra are co-added a number, N, of times so as to improve signal-to-noise ratio. (Accordingly, execution may loop back to Step 388 N−1 times.)

Once the spectral data has been acquired in steps 388 and 390, absorption features are identified in Step 392. This step may be skipped if it is known that certain spectral features will always be present (such as, by the nature of the sample) and that they will always occur at certain locations within the spectral data (such as by known successful stabilization of system temperature, gas pressure, laser temperature, laser power and non-linear crystal temperature). Otherwise, if the Step 392 is not skipped, it is preferably performed automatically or in automated fashion—as by software that automatically analyzes the spectral data to determine the presence of peaks and their number and locations, if present. In Step 394, a determination is made as to whether the spectral baseline is sufficiently strong—for instance, as by attaining a certain intensity threshold throughout its span. Failure to attain such a threshold could indicate a misalignment of system optics, such that insufficient light reaches the detector or, possibly, a malfunction of the detector itself. Thus, if the baseline is not sufficiently strong, execution branches to the error step 386. Otherwise, execution proceeds to Step 396, in which a determination is made regarding whether the observed spectral features are as expected. IN this sense, the expectations are that a particular number of peaks will be present and will occur at certain locations within the spectrum. If this not the case, then the laser wavelength may have drifted out of range and a re-calibration may be necessary, thus causing branching to the error step 386.

In Step 398, a polynomial fit is made to the baseline, using points in the data that are sufficiently removed (for instance, two or three peak half-widths) from peak locations. In Step 400, the synthetic fitted baseline is removed from the data so as to generate baseline-corrected data, as by simple point-wise subtraction of the polynomial function from the raw data. In Step 402, synthetic fits to the observed spectral features are calculated using, for instance, least squares fitting of the baseline-corrected data to synthetic Lorentzian or Voigt profiles. In step 404, IR absorbance values (and corresponding concentrations of the target gas species) are calculated based on the areas of the synthetic profiles calculated in step 402. In Step 406, the results are reported or stored, such as by showing a current gas species concentration on a display screen or storing various data and results to a file. Typically, the full method 380 may be repeated continuously—possibly many times a second—so as to provide a continuous of target gas concentration versus time in order to calculate vertical flux as, for instance, by means of Eq. 1.

Figure 17:
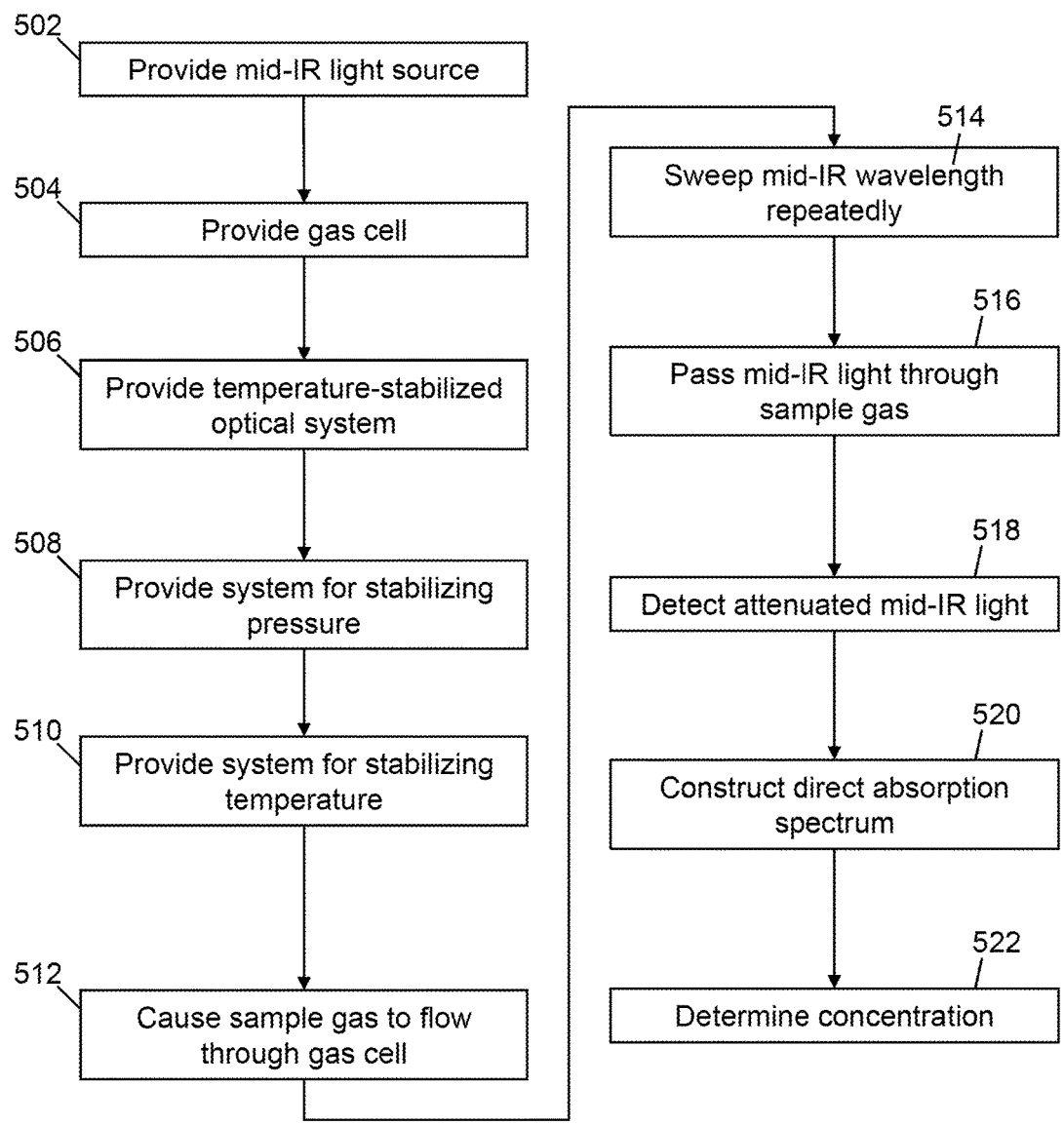
FIG. 17 is a flow chart of a method detecting and measuring the concentration of a gaseous molecular species in accordance with the present teachings.

FIG. 17 is a flow chart of a method 500 for detecting and measuring the concentration of a gaseous molecular species. The molecular species may be measured in a gas sample obtained from an environment—such as an outdoors environment or, possibly, an indoors manufacturing environment—that has its own ambient pressure and temperature. In Step 502, a mid-IR light source is provided. The provided mid-IR light source should have the property that a wavelength of light emitted from the light source may be caused to traverse (or to sweep) across a wavelength range of a rotationally resolved absorption line of the targeted gaseous molecular species. The provided light source may include two (or more) diode lasers which emit light of wavelengths (or, equivalently, frequencies) other than within the near-IR spectral region. For instance, this step may include the steps of: providing a first diode laser capable of providing a first near-IR light comprising a first frequency within a first frequency range; providing a second diode laser capable of providing a second near-IR light comprising a second frequency within a second frequency range, and providing a non-linear crystal operable to receive the first and second near-IR lights and generate the mid-IR light, wherein the frequency of the second near-IR light may be tuned within the second frequency range and wherein the first and second frequency ranges are such that there exists a range of operationally achievable differences between the first and second frequencies that spans a frequency range of the rotationally resolved absorption line.

In Step 504 of the method 500, a gas cell is provided. In Step 506, there is provided a temperature-stabilized optical system to direct the mid-IR light to pass into and through the gas cell and, subsequently, after exiting the gas cell, to a photodetector. As but one example, the temperature stabilized optical system may include a thermally insulated enclosure; components of the optical system within the thermally insulated enclosure; a heater or heater either within the thermally insulated enclosure or within an aperture of the enclosure for providing heat to or transferring heat into or out of the thermally insulated enclosure; a temperature sensor with the thermally insulated enclosure; and temperature controller circuitry in electrical communication with the temperature sensor and the thermoelectric element, the temperature controller circuitry providing a current to the thermoelectric element based on an electronic signal received from the temperature sensor. As previously described, the heat exchanger may include a thermoelectric element within an aperture of the thermally insulated enclosure and, possibly, a first and a second heat sink and fan assembly in thermal contact with the thermoelectric element and disposed outside of and within the thermally insulated enclosure, respectively.

In Step 508 of the method 500, a system for stabilizing the pressure of a sample gas flowing through the gas cell at a pressure less than the ambient pressure to within one torr (1 Torr) is provided. As but one example, the provided system may include a sample gas inlet port at a first end of the gas cell in fluid communication with the environment; a sample gas outlet port at a second end of the gas cell; a vacuum pump in fluidic communication with the sample gas outlet port and with a sample gas exhaust port; a pressure transducer in fluidic communication with the interior of the gas cell; and pressure controller circuitry in electrical communication with the pressure transducer and the vacuum pump, the pressure controller circuitry operable to cause the pumping rate of the vacuum pump to vary based on an electronic signal received from the pressure transducer. Alternatively, the pressure controller circuitry may be in electrical communication with a flow controller, such as a variable gas metering valve, to control the flow rate through—and thus the pressure within—the gas cell.

In Step 510 of the method 500, a system for stabilizing above-ambient temperature of sample gas flowing through sample gas cell to within one degree Kelvin (1° K) is provided. This step may include, for instance, the steps of providing the gas cell within the thermally insulated enclosure; and causing the temperature controller to maintain the interior of the thermally insulated enclosure at the sample gas temperature.

In step 512 of the method 500, the gas sample containing the gaseous molecular species of interest is caused to flow through the gas cell at the sub-ambient sample gas pressure and the above-ambient sample gas temperature. While the gas sample is flowing through in this fashion, the mid-IR light source is operated (Step 514) so that the wavelength of mid-IR light repeatedly sweeps across the wavelength range of the rotationally resolved absorption line. Step 514 may include the repeatedly executed sub-steps of: setting an operating parameter of the light source so as to extinguish the emission of the mid-IR light from the light source; setting the operating parameter so as to cause the light source to emit light comprising a starting wavelength; and varying the operating parameter so as to cause the emitted mid-IR light wavelength to continuously vary from the starting wavelength to an ending wavelength, wherein the starting wavelength and the ending wavelength span the wavelength range of the rotationally resolved absorption line. Optionally, a fourth sub-step may be added, this latter sub-step comprising varying the operating parameter so as to cause the emitted mid-IR light wavelength to continuously vary from the ending wavelength back to the starting wavelength. Obviously, many other variations of or augmentations to this sequence of sub-steps are possible. In Step 516 of the method 500, the optical system is operated so as to cause the emitted mid-IR light to pass through and be attenuated by the sample gas in the gas cell and so as to cause the attenuated mid-IR light to pass to the photodetector. This step is performed while the gas sample is flowing through the gas cell (Step 512) and while the wavelength is being swept across (or caused to traverse) the absorption line (Step 514).

In Step 518 of the method 500, the attenuated mid-IR light is detected by a detector at each of a plurality of discrete data points, each such data point corresponding to a respective wavelength during a wavelength sweep across the absorption line (Step 514) while the gas sample is flowing through the gas cell (Step 512) and while the mid-IR light passes through and is attenuated by the sample gas in the gas cell (Step 516). Step 518 causes repeated generation of spectra such as shown in FIG. 11B, each such spectrum comprising the plurality of data points—for example pairs of numbers consisting of a number representing time and a number representing the detector signal at that respective time—generated during a single wavelength sweep or traverse across the absorption line of interest. The spectra obtained during each of the repeated sweeps may be added together (i.e., co-added) so as to produce a resulting spectrum with improved signal-to-noise characteristics.

In subsequent Step 520, a direct absorption spectrum of the absorption line is constructed using the plurality of data points. Step 520 may include the sub-steps of: determining a null detector response corresponding to no emission of the mid-IR light (for instance, the quantity $V_{offset}$ in FIG. 11B); subtracting the null detector response pointwise from the plurality of data points; fitting a model polynomial baseline (for instance, line 308 in FIG. 11B) using a subset of the plurality of data points outside of the wavelength range of the rotationally resolved absorption line or lines; and subtracting, pointwise, the value of each of the plurality of data points from the value of the fitted polynomial calculated at the wavelength of each respective data point. These sub-steps may be performed using the co-added data such as is shown in FIG. 12A. The result is a corrected detector signal comprising a direct absorption spectrum as illustrated in FIG. 12B. Finally, in Step 522, a concentration of the gaseous molecular species is determined from the direct absorption spectrum. This step may include fitting model curves to a transmittance spectrum as shown in FIG. 12B and using parameters of the fitted model curves—for instance amplitude of or total area encompassed by (e.g., a mathematical integral) a fitted model curve.

CONCLUSION

A novel gas sensor system, methods for sensing gaseous species and methods for operating a gas sensor system have been disclosed. Examples of species that the gas sensor can measure include (but are not limited to): methane, $CO_2$ (and isotopes of $CO_2$), water vapor, CO, $N_2O$, and COS. The gas samples used for this measurement typically are made up of a mixture of numerous gases; for instance, measuring the concentration of a component of air is a common application. As one example, the ambient concentration of methane in air is around 2,000 parts-per-billion (ppb), and using a gas sensor in accordance with the present teachings, the methane concentration in air can be determined with a precision of approximately ±1 ppb. With signal averaging over longer time intervals, the sensor can achieve detection sensitivities down to about 50 parts-per-trillion (ppt).

A gas sensor in accordance with the present teachings is capable of measuring absorption features on the order of 1 part in 10,000 (0.01%). To achieve this high level of sensitivity, the sensor incorporates numerous features that ensure a stable and accurate measurement. Various elements of the gas sensor used to achieve this high sensitivity may include the following: (a) a narrowband, tunable mid-infrared laser source; (b) a temperature- and pressure-stabilized multi-reflecting gas cell; (c) a temperature-stabilized optical detector; (d) a vacuum pump, pressure sensor and flow-controller for providing the gas cell temperature and pressure stabilization; (e) an optical system for routing mid-infrared laser light from the laser source to the gas cell and for receiving the light, after its passage through the gas cell, back from the gas cell and for routing the light to the detector; (f) an insulated temperature-stabilized thermal enclosure enclosing the mid-infrared laser source, the gas cell, the optical system and the detector laser wavelength; and (g) a computer or other logic controller or controllers for acquiring and analyzing light intensity data from the light detector, receiving temperature and pressure information from the pressure sensors, and stabilizing temperature and pressure. The computer or logic controller or controllers may include methods for monitoring and stabilizing the laser wavelength, for system calibration, for monitoring temperatures, pressures and laser output, and for acquiring, displaying and storing data.

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative product and method and illustrative examples shown and described. Accordingly, departures may be made from such details without departing from the scope of the general inventive concept.

What is claimed is:

1. A gas sensor system for detecting and measuring the concentration of a gaseous molecular species within an environment having an ambient temperature and an ambient pressure, the system comprising:
   a gas cell operable so as to receive the sample gas from the environment;
   a vacuum system fluidically coupled to the gas cell operable to maintain the sample gas within the gas cell at a predetermined pressure less than the ambient pressure;
   a pressure sensor operable to sense a pressure of the sample gas within the gas cell;
   a thermally insulated enclosure having the gas cell disposed therein;
   a heat source or heat exchanger operable to influence a temperature of the interior of the thermally insulated enclosure;
   a laser module within the thermally insulated enclosure;
   a light source disposed within the laser module and operable to provide a mid-infrared (mid-IR) light into the gas cell so as to be transmitted through the sample gas therein, wherein a wavelength of the mid-IR light coincides with a rotationally resolved absorption line of the gaseous molecular species;
   an optical module within the thermally insulated enclosure that is optically coupled to the gas cell;
   a photodetector disposed within the optical module operable to receive the mid-IR light transmitted through the sample gas in the gas cell;
   an optical fiber coupled to the laser module and to the optical module, wherein the optical fiber is operable to direct the mid-1R light from the light source into the optical module; and
   a control system electronically coupled to the vacuum system and to the pressure sensor operable to maintain the sample gas within the gas cell at the predetermined pressure to within one torr (1 Torr).

2. A gas sensor system for detecting and measuring the concentration of a gaseous molecular species within an environment having an ambient temperature and an ambient pressure, the system comprising:
    a gas cell operable so as to receive the sample gas from the environment;
    a vacuum system fluidically coupled to the gas cell operable to maintain the sample gas within the gas cell at a predetermined pressure less than the ambient pressure;
    a pressure sensor operable to sense a pressure of the sample gas within the gas cell;
    a thermally insulated enclosure having the gas cell disposed therein;
    a heat source or heat exchanger operable to influence a temperature of the interior of the thermally insulated enclosure;
    a light source operable to provide a mid-infrared (mid-IR) light into the gas cell so as to be transmitted through the sample gas therein, wherein a wavelength of the mid-IR light coincides with a rotationally resolved absorption line of the gaseous molecular species;
    a laser module within the thermally insulated enclosure comprising:
        a first and a second laser operable to provide, respectively, a first near-infrared (near-IR) light having a first wavelength and a second near-IR light having a second wavelength; and
        a wavelength division multiplexer (WDM) optically coupled to the first laser and to the second laser and operable to receive the first and second near-IR lights therefrom;
    an optical fiber having a first end and a second end, the first end optically coupled to the WDM and operable to receive the first and second near-IR lights therefrom;
    a photodetector operable to receive the mid-IR light transmitted through the sample gas in the gas cell;
    an optical module within the thermally insulated enclosure and having the photodetector disposed therein comprising:
        an optically non-linear crystal optically coupled to the second end of the optical fiber and operable to receive the first and second near-IR lights therefrom and to generate the mid-IR light by difference frequency generation; and
        an optical filter optically coupled to the non-linear crystal and operable to transmit the mid-IR light while blocking transmission of the first and second near-IR lights,
        wherein the optical filter is optically coupled to the gas cell such that, in operation, the mid-IR light is transmitted through the optical filter to the gas cell; and
    a control system electronically coupled to the vacuum system and to the pressure sensor operable to maintain the sample gas within the gas cell at the predetermined pressure to within one torr (1 Torr).

3. A gas sensor system as recited in claim 2, wherein the gas cell is fluidically coupled to the optical module such that, in operation, the sample gas flows from the gas cell into the optical module.

4. A gas sensor system as recited in claim 2, further comprising:
    a temperature sensor operable to sense a temperature of the sample gas within the gas cell; and
    a control system electronically coupled to the heat source or heat exchanger and to the temperature sensor operable to maintain the sample gas within the gas cell at a predetermined temperature to within one degree Kelvin (1° K).

5. A gas sensor system as recited in claim 2, wherein the first and second lasers respectively comprise first and second diode lasers, further comprising:
    a laser diode current driver operable to repeatedly modulate a drive current supplied to one of the first and second diode lasers such that a wavelength of the mid-1R light repeatedly traverses across a wavelength range of the rotationally resolved optical absorption line;
    a digitizer electronically coupled to an output of the photodetector such that an output of the photodetector is digitized at each of a plurality of discrete time points during each modulation of the drive current so as to generate a plurality of digital detector signal values corresponding to a direct absorption spectrum; and
    a digital memory storage device operable to store the plurality of digital detector signal values.

6. A gas sensor system for detecting and measuring the concentration of a gaseous molecular species within an environment having an ambient temperature and an ambient pressure, the system comprising:
    a gas cell operable so as to receive the sample gas from the environment;
    a vacuum system fluidically coupled to the gas cell operable to maintain the sample gas within the gas cell at a predetermined pressure less than the ambient pressure;
    a pressure sensor operable to sense a pressure of the sample gas within the gas cell;
    a thermally insulated enclosure having the gas cell disposed therein;
    a heat source or heat exchanger operable to influence a temperature of the interior of the thermally insulated enclosure;
    a light source operable to provide a mid-infrared (mid-IR) light into the gas cell so as to be transmitted through the sample gas therein, wherein a wavelength of the mid-IR light coincides with a rotationally resolved absorption line of the gaseous molecular species;
    a laser module within the thermally insulated enclosure comprising:
        a first laser operable to provide a first near-ER light having a first wavelength; and
        a second laser operable to provide a second near-IR light having a second wavelength;
    a first optical fiber having a first end and a second end, the first end optically coupled to the first laser and operable to receive the first near-IR light therefrom;
    a second optical fiber having a first end and a second end, the first end optically coupled to the second laser and operable to receive the second near-IR light therefrom;
    a photodetector operable to receive the mid-IR light transmitted through the sample gas in the gas cell;
    an optical module within the thermally insulated enclosure and having the photodetector disposed therein comprising:
        a beam combiner or multiplexer optically coupled to the second end of the first optical fiber and to the second end of the second optical fiber, and operable to receive first and second near-IR lights from the first and second optical fibers, respectively;
        an optically non-linear crystal optically coupled to beam combiner or multiplexer and operable to receive the first and second near-IR lights therefrom and to generate the mid-IR light by difference frequency generation; and an optical filter optically coupled to the non-linear crystal and transmitting the mid-IR light and blocking transmission of the first and second near-IR lights, wherein the optical filter is optically coupled to the gas cell; and a control system electronically coupled to the vacuum system and to the pressure sensor operable to maintain the sample gas within the gas cell at the predetermined pressure to within one torr (1 Torr).

7. A gas sensor system as recited in claim 6, wherein the gas cell is fluidically coupled to the optical module such that, in operation, the sample gas flows from the gas cell into the optical module.

8. A gas sensor system as recited in claim 6, further comprising:

a temperature sensor operable to sense a temperature of the sample gas within the gas cell; and a control system electronically coupled to the heat source or heat exchanger and to the temperature sensor operable to maintain the sample gas within the gas cell at a predetermined temperature to within one degree Kelvin (1° K).

9. A gas sensor system as recited in claim 6, wherein the first and second lasers respectively comprise first and second diode lasers, further comprising:

a laser diode current driver operable to repeatedly modulate a drive current supplied to one of the first and second diode lasers such that a wavelength of the mid-IR light repeatedly traverses across a wavelength range of the rotationally resolved optical absorption line;

a digitizer electronically coupled to an output of the photodetector such that an output of the photodetector is digitized at each of a plurality of discrete time points during each modulation of the drive current so as to generate a plurality of digital detector signal values corresponding to a direct absorption spectrum; and a digital memory storage device operable to store the plurality of digital detector signal values.

10. A gas sensor system for detecting and measuring the concentration of a gaseous molecular species within an environment having an ambient temperature and an ambient pressure, the system comprising:

a gas cell operable so as to receive the sample gas from the environment;

a vacuum system fluidically coupled to the gas cell operable to maintain the sample gas within the gas cell at a predetermined pressure less than the ambient pressure;

a pressure sensor operable to sense a pressure of the sample gas within the gas cell;

a thermally insulated enclosure having the gas cell disposed therein;

a heat source or heat exchanger operable to influence a temperature of the interior of the thermally insulated enclosure;

a light source within the thermally insulated enclosure operable to provide a mid-infrared (mid-IR) light into the gas cell so as to be transmitted through the sample gas therein, wherein a wavelength of the mid-IR light coincides with a rotationally resolved absorption line of the gaseous molecular species, the light source comprising:

a first and a second diode laser operable to provide, respectively, a first near-infrared (near-IR) light having a first wavelength and a second near-IR light having a second wavelength;

an optically non-linear crystal optically coupled to both the first and the second diode laser so as to receive both the first and the second near-IR lights and to generate the mid-IR light by difference frequency generation; and an optical filter optically coupled to the non-linear crystal and operable to transmit the mid-IR light while blocking transmission of the first and second near-IR lights, wherein the optical filter is optically coupled to the gas cell such that, in operation, the mid-IR light is transmitted through the optical filter to the gas cell;

a photodetector within the thermally insulated enclosure operable to receive the mid-IR light transmitted through the sample gas in the gas cell; and a control system electronically coupled to the vacuum system and to the pressure sensor operable to maintain the sample gas within the gas cell at the predetermined pressure to within one torr (1 Torr).

11. A gas sensor system as recited in claim 10, further comprising:

a laser diode current driver operable to repeatedly modulate a drive current supplied to one of the first and second diode lasers such that a wavelength of the mid-IR light repeatedly traverses across a wavelength range of the rotationally resolved optical absorption line;

a digitizer electronically coupled to an output of the photodetector such that an output of the photodetector is digitized at each of a plurality of discrete time points during each modulation of the drive current so as to generate a plurality of digital detector signal values corresponding to a direct absorption spectrum; and a digital memory storage device operable to store the plurality of digital detector signal values.

12. A gas sensor system as recited in claim 1, wherein the wavelength of the mid-IR light is within the range of approximately 3.0 microns to 4.8 microns.

13. A gas sensor system as recited in claim 12, wherein the gaseous molecular species is methane ($CH_4$) and a center wavelength of the rotationally resolved absorption line is within the range of approximately 3.2 microns to 3.4 microns.

14. A gas sensor system as recited in claim 12, wherein the gaseous molecular species is chosen from the group consisting of carbon monoxide (CO), nitrous oxide ($N_2O$) and carbon dioxide ($CO_2$) and a center wavelength of the rotationally resolved absorption line is within the range of approximately 4.2 microns to 4.7 microns.

15. A gas sensor system as recited in claim 12, wherein the gaseous molecular species is carbon monoxide (CO) and a center wavelength of the rotationally resolved absorption line is within the range of approximately 4.57 microns to 4.65 microns.

16. A gas sensor system as recited in claim 12, wherein the gaseous molecular species is nitrous oxide ($N_2O$) and a center wavelength of the rotationally resolved absorption line is within the range of approximately 4.510 microns to 4.555 microns.

17. A gas sensor system as recited in claim 1, further comprising:

a temperature sensor operable to sense a temperature of the sample gas within the gas cell; and a control system electronically coupled to the heat source or heat exchanger and to the temperature sensor operable to maintain the sample gas within the gas cell at a predetermined temperature to within one degree Kelvin (1° K).

18. A gas sensor system as recited in claim 17, wherein the predetermined temperature is greater than the ambient temperature.

19. A gas sensor system as recited in claim 17, wherein the predetermined temperature is within a range between about 30° C. to about 40° C.

20. A gas sensor system as recited in claim 1, wherein the heat source or heat exchanger comprises a thermoelectric element disposed within an aperture of the thermally insulated enclosure that is operable to either transfer heat into or out of the thermally insulated enclosure.

21. A gas sensor system as recited in claim 20, further comprising a first and a second heat sink and fan assembly in thermal contact with the thermoelectric element and disposed outside of and within the thermally insulated enclosure, respectively.

22. A gas sensor system as recited in claim 1, wherein the gas cell is fluidically coupled to the optical module such that, in operation, the sample gas flows from the gas cell into the optical module.

23. A gas sensor system as recited in claim 10, wherein the gas cell is fluidically coupled to the optical module such that, in operation, the sample gas flows from the gas cell into the optical module.

* * * * *

UNITED STATES PATENT AND TRADEMARK OFFICE
CERTIFICATE OF CORRECTION

| | | |
|---|---|---|
| PATENT NO. | : 10,107,751 B2 | Page 1 of 1 |
| APPLICATION NO. | : 15/595366 | |
| DATED | : October 23, 2018 | |
| INVENTOR(S) | : James J Scherer et al. | |

It is certified that error appears in the above-identified patent and that said Letters Patent is hereby corrected as shown below:

In the Claims

Claim 1, Column 38, Line 60:
Replace "direct the mid-1R light"
With --direct the mid-IR light--

Claim 5, Column 40, Line 10:
Replace "mid-1R light"
With --mid-IR light--

Claim 6, Column 40, Line 46:
Replace "to provide a first near-ER light"
With --to provide a first near-IR light--

Signed and Sealed this
Third Day of September, 2019

Andrei Iancu
*Director of the United States Patent and Trademark Office*